US008242255B2

(12) United States Patent
Levy

(10) Patent No.: US 8,242,255 B2
(45) Date of Patent: *Aug. 14, 2012

(54) ANTISENSE OLIGONUCLEOTIDES AGAINST CPLA$_2$, COMPOSITIONS AND USES THEREOF

(75) Inventor: Rachel Levy, Omer (IL)

(73) Assignees: Mor Research Applications Ltd., Tel-Aviv (IL); Ben Gurion University of the Negev Research and Development Authority, Beer-Sheva (IL)

( * ) Notice: Subject to any disclaimer, the term of this patent is extended or adjusted under 35 U.S.C. 154(b) by 105 days.

This patent is subject to a terminal disclaimer.

(21) Appl. No.: 11/568,169

(22) PCT Filed: Apr. 17, 2005

(86) PCT No.: PCT/IL2005/000399
§ 371 (c)(1),
(2), (4) Date: Aug. 19, 2007

(87) PCT Pub. No.: WO2005/101968
PCT Pub. Date: Nov. 3, 2005

(65) Prior Publication Data
US 2008/0287380 A1 Nov. 20, 2008

(30) Foreign Application Priority Data

Apr. 22, 2004 (IL) .......................... 161579

(51) Int. Cl.
C07H 21/04 (2006.01)
C12N 15/11 (2006.01)
C12Q 1/68 (2006.01)
C12N 5/00 (2006.01)

(52) U.S. Cl. .................... 536/24.5; 536/23.1; 514/44 A; 435/6.1; 435/375

(58) Field of Classification Search .................. None
See application file for complete search history.

(56) References Cited

U.S. PATENT DOCUMENTS

| 5,998,148 | A | 12/1999 | Bennett |
| 6,008,311 | A | 12/1999 | Sakamoto et al. |
| 6,008,334 | A | 12/1999 | Hanna |
| 6,008,344 | A | 12/1999 | Bennett et al. |
| 6,797,708 | B2 | 9/2004 | McKew et al. |
| 2002/0165119 | A1 | 11/2002 | Leff |
| 2006/0014759 | A1 | 1/2006 | McKew et al. |
| 2010/0204298 | A1 | 8/2010 | Levy |

FOREIGN PATENT DOCUMENTS

| EP | 0260032 | 3/1988 |
| EP | 260032 | 12/1994 |
| WO | WO 00/50438 | 8/2000 |
| WO | WO 02/060535 | 8/2002 |
| WO | WO-02/060535 | 10/2003 |
| WO | WO 2005/101968 | 11/2005 |
| WO | WO 2006/128142 | 11/2006 |
| WO | WO 2008/038267 | 4/2008 |

OTHER PUBLICATIONS

Laktionov et al., Knock down of cytosolic phospholipase A2: an antisense oligonucleotide having a nuclear localization binds a C-terminal motif of glyceraldehyde-3-phosphate dehydrogenase, 2004, Biochimica et Biophysica Acta, vol. 1636, pp. 129-135.*
Sohail et al., Selecting optimal antisense reagents, 2000, Advanced Drug Delivery Reviews, vol. 44, pp. 23-34.*
Allawi et al., Mapping of RNA accessible sites by extension of random oligonucleotide libraries with reverse transcriptase, 2001, RNA, vol. 7, pp. 314-327.*
Scherr et al., RNA accessibility prediction: a theoretical approach is consistent with experimental studies in cell extracts, 2000, Nucleic Acids Research, vol. 28, pp. 2455-2461.*
Chalk et al., Computational antisense oligo prediction with a neural network model, 2002, Bioinformatics, vol. 18, pp. 1567-1575.*
Greenbaum, Dov et al. (2003) "Comparing Protein Abundance and mRNA Expression Levels on a Genomic Scale" Genome Biology, 4:117.
Zhang, Hong et al. (1997) "Antisense Inhibition of the Photosystem I Antenna Protein Lhca4 in *Arabidopsis thaliana*" Plant Physiol., 115 pp. 1525-1531.
Anderson, K.M. et al., J. Biol. Chem., 1997, pp. 30504-30511, vol. 272(48).
Bendele, A.M. et al., Arthritis & Rheumatism, 2000, pp. 2648-2658, vol. 43.
Dana, R. et al., J. Biol. Chem., 1998, pp. 441-445, vol. 273.
Dana, R. et al., Biochem J., 1994, pp. 217-223, vol. 297.
Dias, N. and Stein, C.A., Eur. J. Pharmac. and Biopharmac., 2002, pp. 263-269, vol. 54.
Gijon, M. A. et al., J. Biol. Chem., 2000, p. 20146, vol. 275.
Griffoni, C. et al., Biochimica et Biophysica Acta, 2001, pp. 32-46, vol. 1530(1).
Hazan et al., Biochem J., 1997, pp. 867-876, vol. 326.
Hazan-Halevy, I. et al., J. Biol. Chem., 2000, pp. 12416-12426, vol. 275.
Jaeger, J.A., Methods Enzymol., 1989, pp. 281-306, vol. 183.
Jansen, B. et al., Lancet, 2000, pp. 1728-1733, vol. 356.
Kalyvas et al., Neuron, 2004, pp. 323-335, vol. 41.
Kiaei et al., Journal of Neurochemistry, 2005, pp. 403-441, vol. 93.
Levy, R. et al., J. Biol. Regul. Homeost. Agents, 1989, pp. 71-78, vol. 3(2).
Levy, R et al., Biochim. Biophys. Acta., 1994, pp. 253-260, vol. 1220.
Levy, R. et al., Biochim. Biophys. Acta., 1994, pp. 261-235, vol. 1220.
Levy, R. et al., Blood, 2000, pp. 660-665, vol. 95.

(Continued)

Primary Examiner — Dana Shin

(57) ABSTRACT

Antisense oligonucleotides against cPLA$_2$ are provided, which are capable of inhibiting cPLA$_2$ expression as well as superoxide production, especially in phagocytes. These antisense oligonucleotides are powerful agents for the treatment of inflammatory conditions, in particular arthritis, as well as in neurodegenerative diseases. The antisense oligonucleotides or compositions comprising the same may be used in methods of treatment of such diseases.

9 Claims, 22 Drawing Sheets
(20 of 22 Drawing Sheet(s) Filed in Color)

OTHER PUBLICATIONS

Levy, R. and Malech, H., J. Immunol., 1991, pp. 3066-3071, vol. 147.
Li, Q. and Cathcart, M.K., J. Biol. Chem., 1997, pp. 2404-2411, vol. 272(4).
Locati, M., J. Biol. Chem., 1996, pp. 6010-6016, vol. 271(11).
Lowenthal, A. and Levy, R., J. Biol. Chem., 1999, pp. 21603-21610, vol. 274.
Marshall, L., J. Biol. Chem., 1997, pp. 759-765, vol. 272(2).
Muthalif, M.M. et al., J. Biol. Chem., 1996, pp. 30149-30157, vol. 271(47).
Persaud, S. J. et al., Diabetes, 2002, pp. 98-104, vol.51(1).
Pessach, I. et al., J. Biol. Chem., 2001, pp. 33495-33503, vol. 276.
Pirollo, K.F. et al., Pharmacology & Therapeutics, 2003, pp. 55-77, vol. 99.
Reisenberg, K. et al., Eur. J. Clin. Invest, 1997, pp. 398-404, vol. 27.
Roshak, A., J. Biol. Chem., 1994, pp. 25999-26005, vol. 269(42).
Rubin, B.B. et al., J. Biol. Chem., 2005, pp. 7519-7529, vol. 280.
Segal, B. H. et al., J. Leukoc. Biol., 2002, p. 410, vol. 71.
Snaked, G. et al., J. Trauma, 1994, pp. 22-29, vol. 37.
Shmelzer, Z. et al., J. Cell Biol., 2003, pp. 683-692, vol. 162.
Stein et al., Nucleic Acid Res., 1988, pp. 3209-3221, vol. 16.
Tarsi-Tsuk, D. and Levy, R., J. Immunol., 1990, pp. 2665-2670, vol. 144.
Tommasini, P.S. et al., Cell Death and Differentiation, 2004, pp. 974-984, vol. 11.
Zhao, X. et al., J. Biol. Chem., 2002, pp. 25385-25392, vol. 277(28).
Communication Pursuant to Article 94(3) EPC Dated Apr. 3, 2008 From the European Patent Office Re. Application No. 05731106.0.
Communication Pursuant to Article 94(3) EPC Dated Jul. 22, 2010 From the European Patent Office Re. Application No. 05731106.0.
Communication Pursuant to Rules 109 and 110 EPC Dated May 24, 2007 From the European Patent Office Re. Application No. 05731106.0.
Examiner's Report Dated Apr. 1, 2009 From the Australian Government, IP Australia Re. Application No. 2005235286.
Examiner's Report Dated Jun. 11, 2010 From the Australian Government, IP Australia Re. Application No. 2005235286.
International Preliminary Report on Patentability Dated Mar. 13, 2007 From the International Bureau of WIPO Re. Application No. PCT/IL2005/000399.
International Preliminary Report on Patentability Dated Mar. 31, 2009 From the International Bureau of WIPO Re. Application No. PCT/IL2007/001164.
International Search Report and the Written Opinion Dated May 21, 2008 From the International Searching Authority Re. Application No. PCT/IL2007/001164.
International Search Report and the Written Opinion Dated Jan. 22, 2007 From the International Searching Authority Re. Application No. PCT/IL2005/000399.
Office Action Dated Sep. 5, 2009 From the Israel Patent Office Re. Application No. 178401.
Office Action Dated Feb. 9, 2009 From the Israel Patent Office Re. Application No. 178764.
Office Action Dated Jul. 9, 2009 From the Israel Patent Office Re. Application No. 178401.
Office Action Dated Nov. 10, 2010 From the Israel Patent Office Re. Application No. 178764.
Official Action Dated Jul. 6, 2010 From the US Patent and Trademark Office Re. U.S. Appl. No. 12/311,419.
Response Dated Nov. 5, 2009 to Office Action of Jul. 9, 2009 From the Israel Patent Office Re. Application No. 178401.
Response Dated Jan. 6, 2011 to Communication Pursuant to Article 94(3) EPC Dated Jul. 22, 2010 From the European Patent Office Re. Application No. 05731106.0.
Response Dated Jan. 6, 2011 to Official Action of Jul. 6, 2010 From the US Patent and Trademark Office Re. U.S. Appl. No. 12/311,419.
Response Dated May 6, 2009 to Office Action of Jan. 14, 2009 From the Israel Patent Office Re. Application No. 178401.
Response Dated Jul. 7, 2008 to Communication Pursuant to Article 94(3) EPC of Apr. 3, 2008 From the European Patent Office Re. Application No. 05731106.0.
Response Dated May 27, 2010 to Examiner's Report of Apr. 1, 2009 From the Australian Government, IP Australia Re. Application No. 2005235286.
Response Dated Jun. 29, 2010 to Examiner's Report of Jun. 11, 2010 From the Australian Government, IP Australia Re. Application No. 2005235286.
Response Dated May 31, 2009 to Office Action of Feb. 9, 2009 From the Israel Patent Office Re. Application No. 178764.
Supplementary European Search Report Dated Nov. 27, 2007 From the European Patent Office Re. Application No. 05731106.0.
Supplementary Partial European Search Report Dated Oct. 9, 2007 From the European Patent Office Re. Application No. 05731106.0.
Translation of Notification of the First Office Action Dated Oct. 9, 2010 From the State Intellectual Property Office of the People's Republic of China Re. Application No. 200580012674.2.
Dong et al. "Cytoplasmic Phospholipase A2 Levels Correlate With Apoptosis in Human Colon Tumorigenesis", Clinical Cancer Research, 11: 2265-2271, Mar. 15, 2005.
Dong et al. "Inverse Association Between Phospholipase A2 and COX-2 Expression During Mouse Colon Tumorigenesis", Carcinogenesis, 24(2): 307-315, 2003.
Dong et al. "Oncogenic Action of Phospholipase A2 in Prostate Cancer", Cancer Letters, 240: 9-16, 2006.
Hong et al. "Deletion of Cytosolic Phospholipase A2 Suppresses Apc[Min]-Induced Tumorigenesis", Proc. Natl. Acad. Sci. USA, PNAS, 98(7); 3935-3939, Mar. 27, 2001.
Kappel et al. "Regulating Gene Expression in Transgenic Animals", Current Opinion in Biotechnology, 3: 548-553, 1992.
Pirianov et al. "Interactions of Vitamin D Analogue CB1093, TNF? and Ceramide on Breast Cancer Cell Apoptosis", Molecular and Cellular Endocrinology, 172: 69-78, 2001.
Rubenstein et al. "Antisense Oligonucleotide Intralesional Therapy for Human PC-3 Prostate Tumors Carried in Athymic Nude Mice", Journal of Surgical Oncology, 62: 194-200, 1996.
Shaik et al. "Enhancement of Antitumor Activity of Docetaxel by Celecoxib in Lung Tumors", International Journal of Cancer, 118: 396-404, 2006.
Shmelzer et al. "Cytosolic Phospholipase A2? Is Targeted to the P47phox-PX Domain of the Assembled NADPH Oxidase Via a Novel Binding Site in Is C2 Domain", The Journal of Biological Chemistry, 283(46): 31898-31908, Nov. 14, 2008.
Van Rossum et al. "Cytosolic Phospholipase A2 and Lipxygenase Are Involved in Cell Cycle Progression in Neuroblastoma Cells", CMLS, Cellular and Molecular Life Sciences, 59(1): 181-188, 2002.
Panel et al. "Cytoplasmic Phospholipase A2 Expression in Human Colon Adenocarcinoma Is Correlated With Cyclooxygenase-2 Expression and Contributes to Prostaglandin E2 Production", Cancer Letters, 243: 255-263, 2006.
Patel et al. "Cytosolic Phospholipase A2-α: A Potential Therapeutic Target for Prostate Cancer", Clinical Cancer Research, 14(24): 8070-8079, Dec. 15, 2008.
Weiser-Evans et al. "Depletion of Cytosolic Phospholipase A2 in Bone Marrow-Derived Macrophages Protects Against Lung Cancer Progression and Metastasis", Cnacer Research, 69(5): 1733-1738, Mar. 1, 2009.
Official Action Dated Feb. 11, 2011 From the US Patent and Trademark Office Re. U.S. Appl. No. 12/311,419.
Response Dated Jan. 12, 2011 to Office Action Dated Sep. 5, 2009 From the Israel Patent Office Re. Application No. 178401.
Anderson et al. "Cytosolic 85-kDa Phospholipase A2-Mediated Release of Arachidonic Acid Is Critical for Proliferation of Vascular Smooth Muscle Cells", The Journal of Biological Chemistry, XP002478503, 272(48): 30504-30511, Nov. 28, 1997.
Bendele et al. "Combination Benefit of Treatment With the Cytokine Inhibitors Interleukin-1 Receptor Antagonist and PEGylated Soluble Tumor Necrosis Factor Receptor Type I in Animal Models of Rheumatoid Arthritis", Arthritis & Rheumatism, 43(12): 2648-2659, Dec. 2000.
Dana et al. "Essential Requirement of Cytosolic Phospholipase A2 for Activation of the Phagocyte NADPH Oxidase", The Journal of Biological Chemistry, 273(1): 441-445, Jan. 2, 1998.

Dana et al. "The Requirement for Phospholipase A2 for Activation of the Assembled NADPH Oxidase in Human Neutrophils", Biochemistry Journal, 297: 217-223, 1994.
Dias et al. "Potential Roles of Antisense Oligonucleotides in Cancer Therapy. The Example of Bcl-2 Antisense Oligonucleotides", European Journal of Pharmaceutics and Biopharmaceutics, 54: 263-269, 2002.
Gij?n. et al. "Cytosolic Phospholipase A2 Is Required for Macrophage Arachidonic Acid Release by Antagonists That Do and Do Not Mobilize Calcium", The Journal of Biological Chemistry, 275(26): 20146-20156, Jun. 30, 2000.
Greenbaum et al. "Comparing Protein Abundance and mRNA Expression Levels on a Genomic Scale", Genome Biology, 4(9/Art. 117): 117.1-117.8, 2003.
Griffoni et al. "The Rossmann Fold of Glyceraldehyde-3-Phosphate Dehydrogenase (GAPDH) Is a Nuclear Docking Site for Antisense Oligonucleotides Containing A TAAAT Motif", Biochimica et Biophysica Acta, XP002452585, 1530(1): 32-46, Jan. 15, 2001. Relevant to Inventions 1, 2, 5.
Hazan et al. "Cytosolic Phospholipase A2 and its Mode of Activation in Human Nutrophils by Opsonized Zymosan. Correlation Between 42/44 kDa Mitogen-Activated Protein Kinase, Cytosolic Phospholipase A2 and NADPH Oxidase", Biochemistry Journal, 326: 867-876, 1997.
Hazan-Halevy et al. "The Requirement of Both Extracellular Regulated Kinase and P38 Mitogen-Activated Protein Kinase for Stimulation of Cytosolic Phospholipase A2 Activity by Either Fc?RIIA or FC?RIIIB in Human Neutrophils. A Possible Role for Pyk2 But Not for the Grb2-Sos-Shc Complex", The Journal of Biological Chemistry, 275(17): 12416-12423, Apr. 28, 2000.
Jaeger et al. "Predicting Optimal and Suboptimal Secondary Structure for RNA", Methods in Enzymology, 183: 281-306, 1990.
Jansen et al. "Chemosensitisation of Malignant Melanoma by BCL2 Antisense Therapy", The Lancet, 356: 1728-1733, Nov. 18, 2000.
Kalyvas et al. "Cytosolic Phospholipase A2 Plays a Key Role in the Pathogenesis of Multiple Sclerosis-Like Disease", Neuron, XP002414424, 41: 323-335, Feb. 5, 2004. p. 323.
Kiaei et al. Integrative Role of cPLA2 With COX-2 and the Effect of Non-Steriodal Anti-Inflammatory Drugs in a Transgenic Mouse Model of Amyotrophic Lateral Sclerosis, Journal of Neurochemistry, 93: 403-411, 2005. p. 403-404.
Laktionov et al. "Knock Down of Cytosolic Phospholipase A2: An Antisense Oligonucleotide Having a Nuclear Localization Binds A C-Terminal Motif of Glyceraldehyde-3-Phosphate Dehydrogenase", Biochimca et Biophysica Acta, 1636: 129-135, 2004.
Levy et al. "Effect of 1,25-Dihydroxyvitamin D3, Lipopolysaccharide, or Lipoteichoic Acid on the Expression of NADPH Oxidase Components in Cultured Human Monocytes", The Journal of Immunology, 147(9): 3066-3071, Nov. 1, 1991.
Levy et al. "Elevated Cytosolic Phospholipase A2 Expression and Activity in Human Neutrophils During Sepsis", Blood, 95: 660-665, 2000.
Levy et al. "Elevated NADPH-Oxidase Activity in Neutrophils From Bile-Duct-Ligated Rats: Changes in the Kinetic Parameters and in the Oxidase Cytosolic Factor P47", Biochimica et Biophysica Acta, 1220: 261-265, 1994.
Levy et al. "Potential Use of Tuftsin in Treatment of *Candida* Peritonitis in a Murine Model", Journal of Biological Regulators and Homeostatic Agents, 3(2): 71-78, 1989.
Levy et al. "The Requirementof P47 Phosphorylation for Activation of NADPH Oxidase by Opsonized Zymosan in Human Neutrophils", Biochimica et Biophysica Act, 1220: 253-260, 1994.
Li et al. "Selective Inhibition of Cytosolic Phospholipase A2 in Activated Human Monocytes", The Journal of Biological Chemistry, 002924797, 272(4): 2404-2411, Jan. 24, 1997. p. 2406, col.1, § 3-4, Relevant to Inventions 1, 2, 5.
Locati et al. "Inhibition of Monocyte Chemotaxis to C-C Chemokines by Antisense Oligonucleotide for Cytosolic Phospholipase A2", The Journal of Biological Chemistry, 271(11): 6010-6016, Mar. 15, 1996.
Lowenthal et al. "Essential Requirement of Cytosolic Phospholipase A2 for Activation of the H+ Channel in Phagocyte-Like Cells", The Journal of Biological Chemistry, 274(31): 21603-21608, Jul. 30, 1999.
Marshall et al. "Depletion of Human Monocyte 85-kDa Phospholipase A2 Does Not Alter Leukotriene Formation", The Journal of Biological Chemistry, 272(2): 759-765, Jan. 10, 1997.

Muthalif et al. "Calcium/Calmodulin-Dependent Protein Kinase II? Mediates Activation of Mitogen-Activated Protein Kinase and Cytosolic Phospholipase A2 in Norepinephrine-Induced Arachidonic Acid Release in Rabbit Aortic Smooth Muscle Cells", The Journal of Biological Chemistry, 271(47): 30149-30157, Nov. 22, 1996.
Patel et al. "Cytosolic Phospholipase A2-?: A Potential Therapeutic Target for Prostate Cancer", Clinical Cancer Research, 14(24): 8070-8079, Dec. 15, 2008.
Persaud et al. "A Key Role for ?-Cell Cytosolic Phospholipase A2 in the Maintenance of Insulin Stores But Not in the Initiation of Insulin Secretion", Diabetes, XP002452586, 51(1): 98-104, Jan. 2002. Relevant to Inventions 1, 2, 5.
Pessach et al. "Essential Requirement of Cytosolic Phospholipase A2 for Stimulation of NADPH Oxidase-Associated Diaphorase Activity in Granulocyte-Like Cells", The Journal of Biological Chemistry, 276(36): 33495-33503, Sep. 7, 2001.
Pirollo et al. "Antisense Therapeutics: From Theory to Clinical Practice", Pharmacology & Therapeutics, 99: 55-77, 2003.
Riesenberg et al. "Neutrophil Superoxide Release and Interleukin 8 in Acute Myocardial Infarction: Distinction Between Complicated and Uncomplicated States", European Journal of Clinical Investigation, 27: 398-404, 1997.
Roshak et al. "Suppression of Monocyte 85-kDa Phospholipase A2 by Antisense and Effects on Endotoxin-Induced Prostaglandin Biosynthesis", The Journal of Biological Chemistry, 269(42): 25999-26005, Oct. 21, 1994.
Rubin et al. "Cytosolic Phospholipase A2-? Is Necessary for Platelet-Activating Factor Biosynthesis, Efficient Neutrophil-Mediated Bacterial Killing, and the Innate Immune Response to Pulmonary Infection", The Journal of Biological Chemistry, 280(9): 7519-7529, Mar. 4, 2005.
Segal et al. "Thioglycollate Peritonitis in Mice Lacking C5, 5-Lipoxygenase, or P47phox: Complement, Leukotrienes, and Reactive Oxidants in Acute Inflammation", Journal of Leukocyte Biology, 71: 410-416, Mar. 2002.
Shaked et al. "Superoxide Production by Neutrophils From Trauma Patients: Regulation of NADPH Oxidase Activity", The Journal of Trauma, 37(1): 22-29, 1994.
Shmelzer et al. "Unique Targeting of Cytosolic Phosphpolipase A2 to Plasma Membranes Mediated by the NADPH Oxidase in Phagocytes", The Journal of Cell Biology, 162(4): 683-692, Aug. 18, 2003.
Stein et al. "Physicochemical Properties of Phosphorothioate Oligodeoxynucleotides", Nucleic Acids Research, 16(8): 3209-3221, 1988.
Tarsi-Tsuk et al. "Stimulation of the Respiratory Burst in Peripheral Blood Monocytes by Lipoteichoic Acid", The Journal of Immunology, 144(7): 2665-2670, Apr. 1, 1990.
Tommasini et al. "Hydrogen Peroxide Generated at the Level of Mitochondria in Response to Peroxynitrite Promotes U937 Cell Death Via Inhibition of the Cytoprotective Signalling Mediated by Cytosolic Phospholipase A2", Cell Death and Differentiation, 11: 974-984, 2004. p. 974.
Zhang et al. "Antisense Inhibition of the Photosystem I Antenna Protein Lhca4 in *Arabidopsis thaliana*", Plant Physiology, 115: 1525-1531, 1997.
Zhao et al. "Cytosolic Phospholipase A2 (cPLA2) Regulation of Human Monocyte NADPH Oxidase Activity", The Journal of Biological Chemistry, 277(28): 25385-25392, Jul. 12, 2002.
Response Dated Mar. 10, 2011 to Office Action of Nov. 10, 2010 From the Israel Patent Office Re. Application No. 178764.
Office Action Dated Jun. 28, 2011 From the Israel Patent Office Re. Application No. 178764 and Its Translation Into English.
Response Dated Aug. 11, 2011 to Official Action of Feb. 11, 2011 From the US Patent and Trademark Office Re. U.S. Appl. No. 12/311,419.
Neufert et al. "An Inducible Mouse Model of Colon Carcinogenesis for the Analysis of Sporadic and Inflammation-Driven Tumor Progression", Nature Protocols, 2(8): 1998-2004, 2007.
Response Dated Oct. 30, 2011 to Office Action of Jun. 28, 2011 From the Israel Patent Office Re. Application No. 178764.

* cited by examiner

H. cPLA2 mRNA

```
   1 gaattctccg gagctgaaaa aggatcctga ctgaaagcta gaggcattga ggagcctgaa
  61 gattctcagg ttttaaagac gctagagtgc caaagaagac tttgaagtgt gaaaacattt
 121 cctgtaattg aaaccaaaat gtcatttata gatccttacb agcacattat agtggagcac
 181 cagtattccc acaagtttac ggtagtggtg ttacgtgcca ccaaagtgac aaaggggcc
 241 tttggtgaca tgcttgatac tccagatccc tatgtggaac tttttatctc tacaacccct
 301 gacagcagga agagaacaag acatttcaat aatgacataa accctgtgtg gaatgagacc
 361 tttgaattta ttttggatcc taatcaggaa aatgttttgg agattacgtt aatggatgcc
 421 aattatgtca tggatgaaac tctaggaca gcaacattta ctgtatcttc tatgaaggtg
 481 ggagaaaaga aagaagttcc tttatttc aaccaagtca ctgaaatggt tctagaaatg
 541 tctcttgaag tttgctcatg cccagaccta cgatttagta tggctctgtg tgatcaggag
 601 aagactttca gacaacagag aaaagaacac ataagggaga gcatgaagaa actcttgggt
 661 ccaaagaata gtgaaggatt gcattctgca cgtgatgtgc ctgtggtagc catattgggt
 721 tcaggtgggg gtttccgagc catggtggga ttctctggtg tgatgaaggc attatacgaa
 781 tcaggaattc tggattgtgc tacctacgtt gctggtcttt ctggctccac ctggtatatg
 841 tcaaccttgt attctcaccc tgattttcca gagaaagggc cagaggagat taatgaagaa
 901 ctaatgaaaa atgttagcca caatccctct ttacttctca caccagaaa agttaaaaga
 961 tatgttgagt ctttatgaa gaagaaaagc tctggacaac ctgtcacctt tactgacatc
1021 tttgggatgt aataggaga aacactaatt cataatagaa tgaatactac tctgagcagt
1081 ttgaaggaaa aagttaatac tgcacaatgc cctttacctc ttttcacctg tcttcatgtc
1141 aaacctgacg tttcagagct gatgtttgca gattgggttg aatttagtcc atacgaaatt
1201 ggcatggcta aatatggtac tttttatggct cccgacttat ttggaagcaa attttttatg
1261 ggaacagtcg ttaagaagta tgaagaaaac ccttgcatt tcttaatggg tgtctggggc
1321 agtgcctttt ccatattgtt caacagagtt ttgggcgttt ctggttcaca aagcagaggc
1381 tccacaatgg aggaagaatt agaaaatatt accacaaagc atattgtgag taatgatagc
1441 tcggacagtg atgatgaatc acgaacccc aaggcactg aaaatgaaga tgctggaagt
1501 gactatcaaa gtgataatca agcaagttgg attcatcgta tgataatggc cttggtgagt
1561 gattcagctt tattcaatac cagaagga cgtgctggga aggtacacaa cttcatgctg
1621 ggcttgaatc tcaatacatc ttatccactg tctcctttga gtgactttgc cacacaggac
1681 tcctttgatg atgatgaact ggatgcagct gtagcagatc ctgatgaatt tgagcgaata
1741 tatgagcctc tggatgtcaa aagtaaaaag attcatgtag tggacagtgg gctcacattt
1801 aacctgccgt atcccttgat actgagacct cagagagggg ttgatctcat aatctccttt
1861 gacttttctg caaggccaag tgactctagt cctccgttca aggaacttct acttgcagaa
1921 aagtgggcta aaatgaacaa gctccccttt ccaaagattg atccttatgt gtttgatcgg
1981 gaagggctga aggagtgcta tgtctttaaa cccaagaatc ctgatatgga aaagattgc
2041 ccaaccatca tccactttgt tctggccaac atcaacttca gaaagtacaa ggctccaggt
2101 gttccaaggg aaactgagga agagaaagaa atcgctgact tgatatttt tgatgaccca
2161 gaatcaccat tttcaacctt caattttcaa tatccaaatc aagcattcaa aagactacat
2221 gatcttatgc acttcaatac tctgaacaac attgatgtga taaagaagc catggttgaa
2281 agcattgaat atagaagaca gaatccatct cgttgctctg tttcccttag taatgttgag
2341 gcaagaagat ttttcaacaa ggagtttcta agtaaaccca agcatagtt catgtactgg
2401 aaatggcagc agtttctgat gctgaggcag tttgcaatcc catgacaact ggatttaaaa
2461 gtacagtaca gatagtcgta ctgatcatga gagctggct gatactcaaa gttgcagtta
2521 cttagctgca tgaaataat actattataa gttaggtgac aaatgatgtt gattatgtaa
2581 ggatatactt agctacattt tcagtcagta tgaacttcct gatacaaatg tagggatata
2641 tactgtattt ttaaacattt ctcaccaact ttcttatgtg tgttcttttt aaaaattttt
2701 tttcttttaa aatatttaac agttcaatct caataagacc tcgcattatg tatgaatgtt
2761 attcactgac tagatttatt cataccatga gacaacacta ttttattta tatatgcata
2821 tatatacata catgaaataa atacatcaat ataaaaataa aaaaaacgg aattc
```

Fig. 1

Dil. 1st Ab      1:2000

Dil. 2nd Ab.     1:7000

Dil. 1st Ab    1:100     1:250     1:500     1:1000

Dil. 2nd Ab.      1:3300

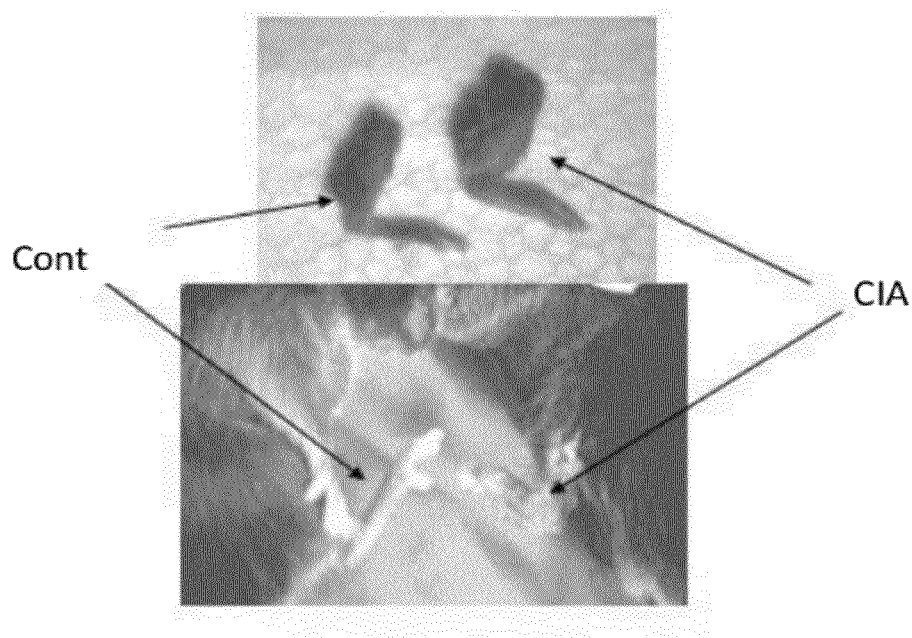
Fig. 10A
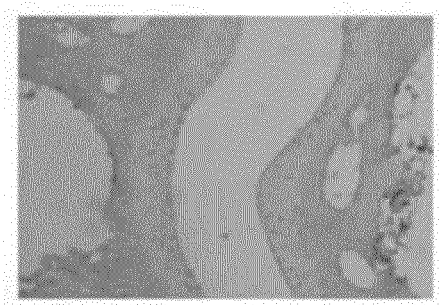 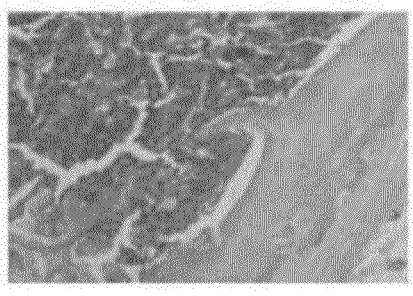
Cont.　　　　　　　　　CIA
Fig. 10B
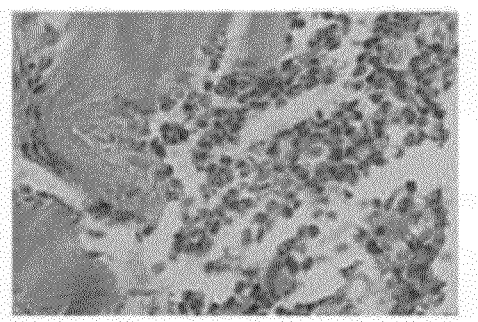
CIA, X400
Fig. 10C

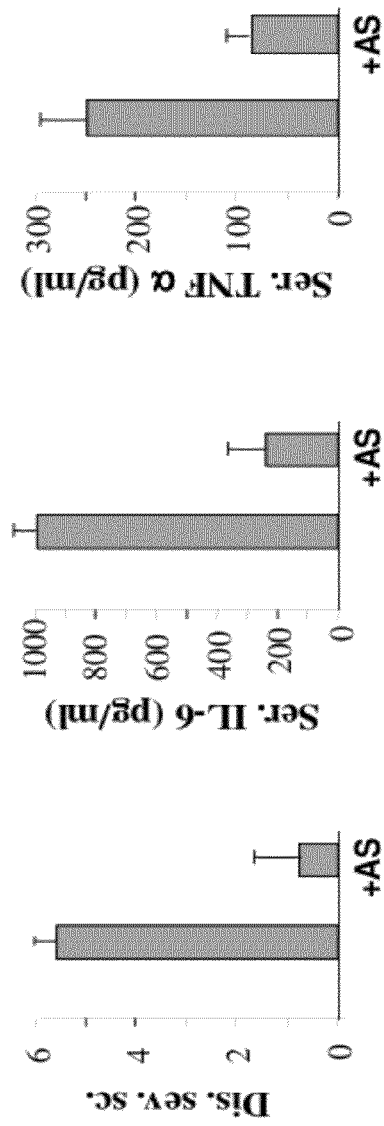
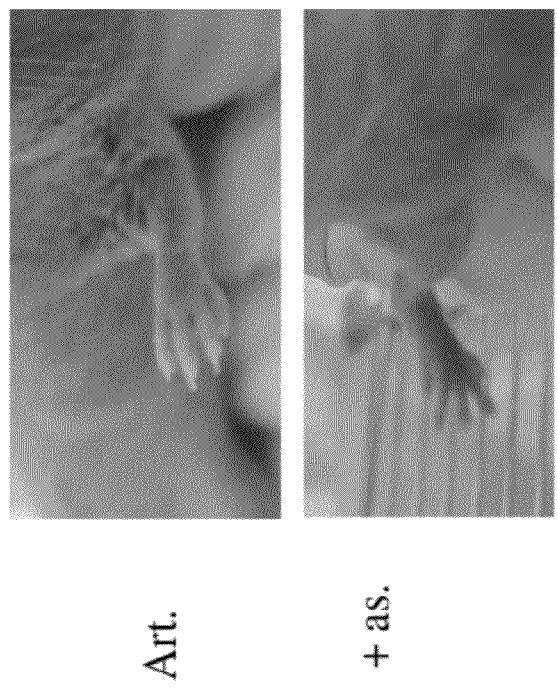
Fig. 11A
Fig. 11B

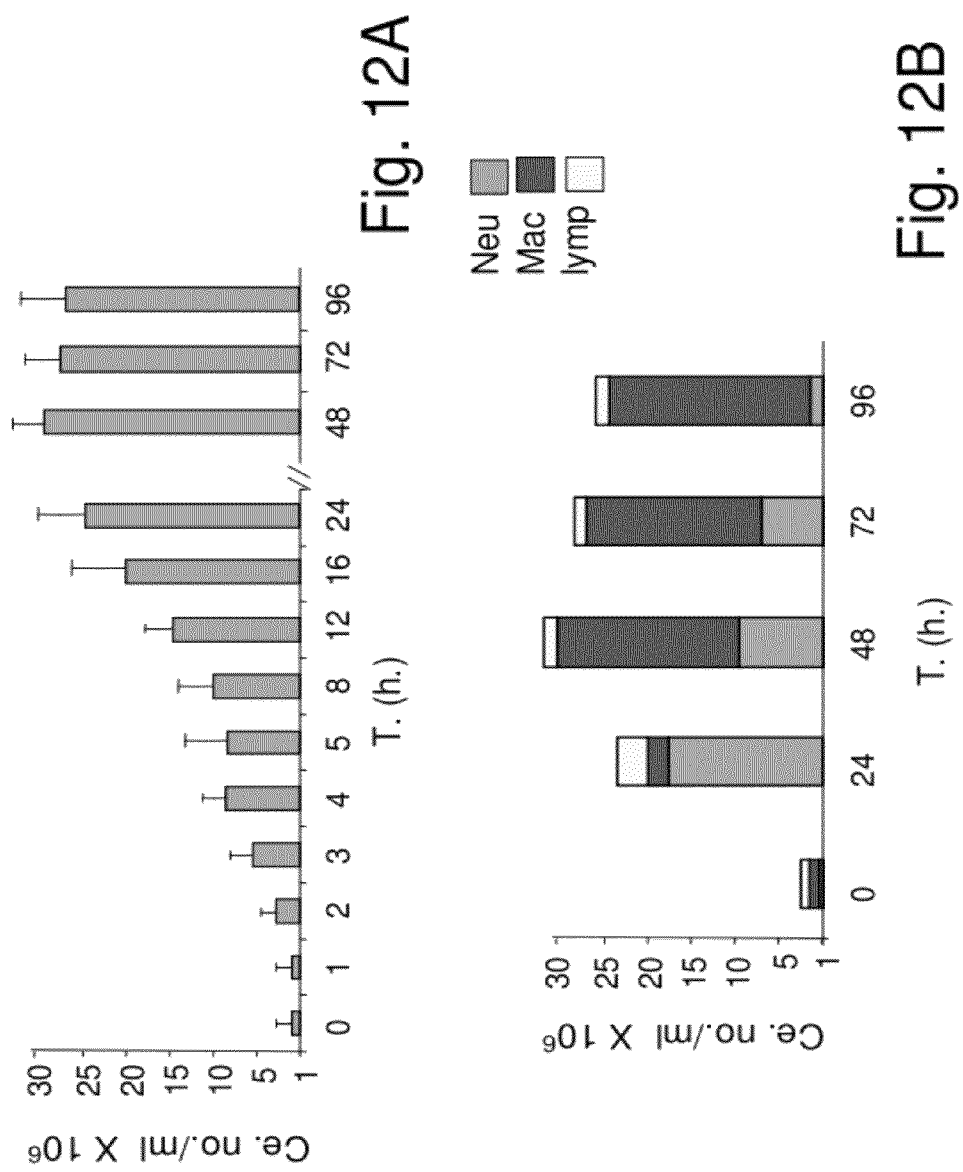

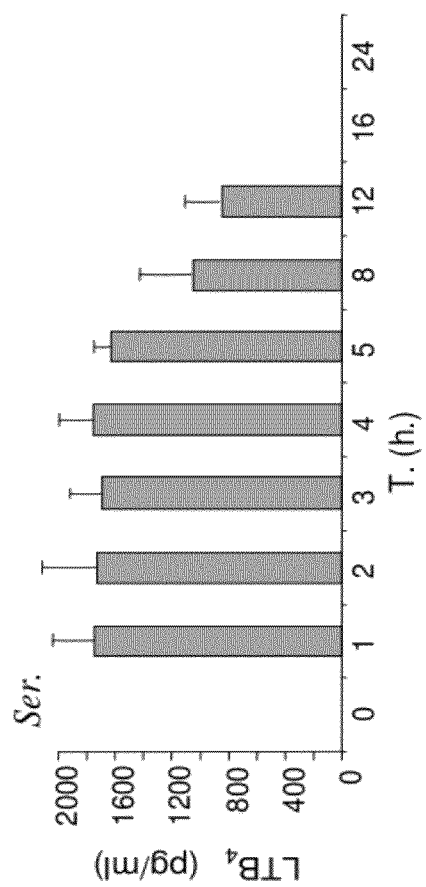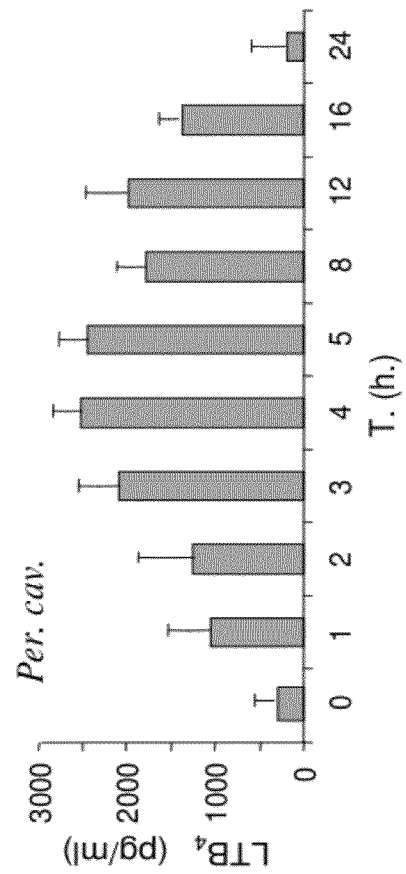

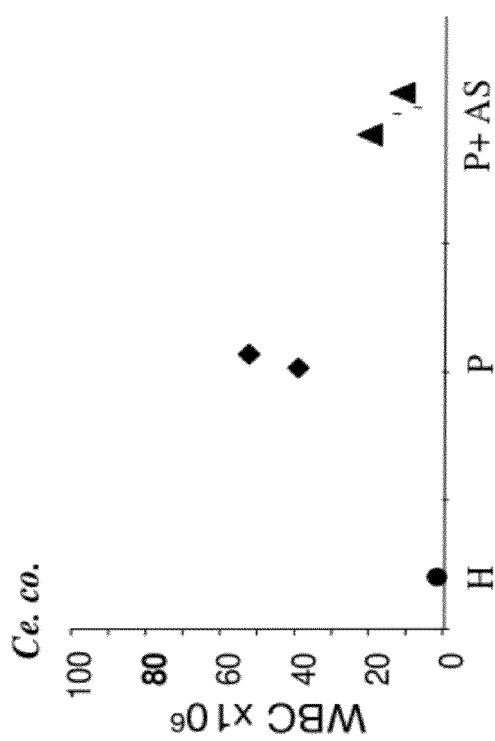

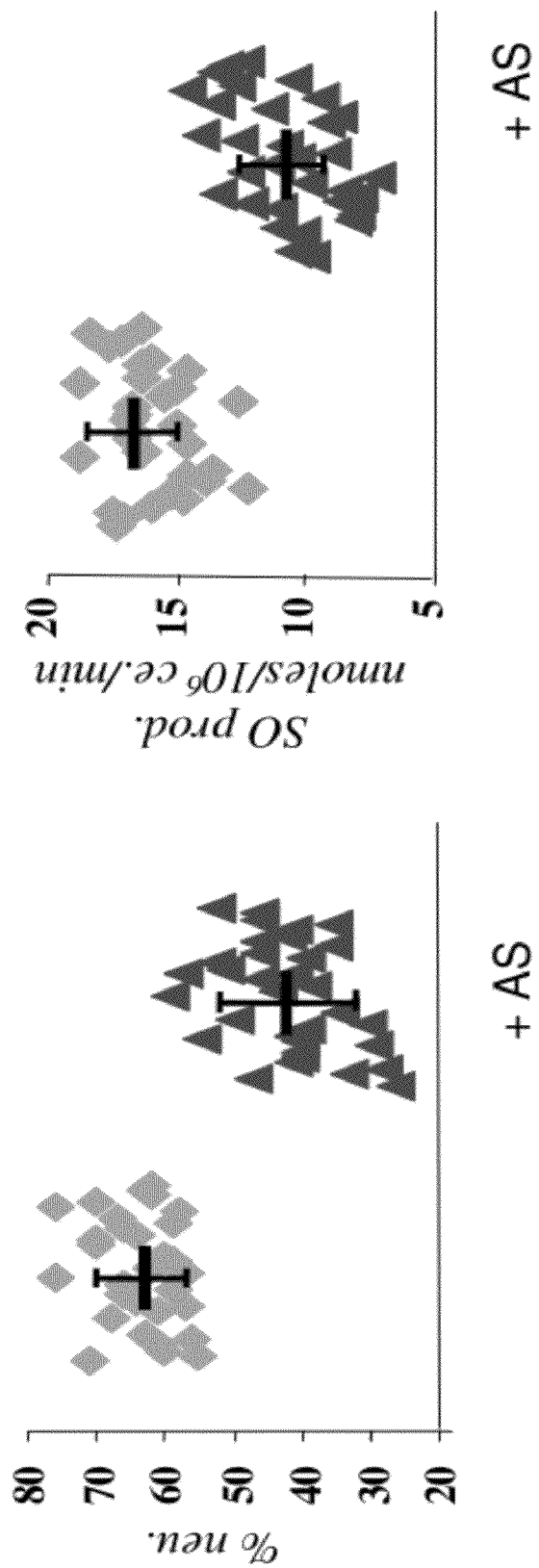

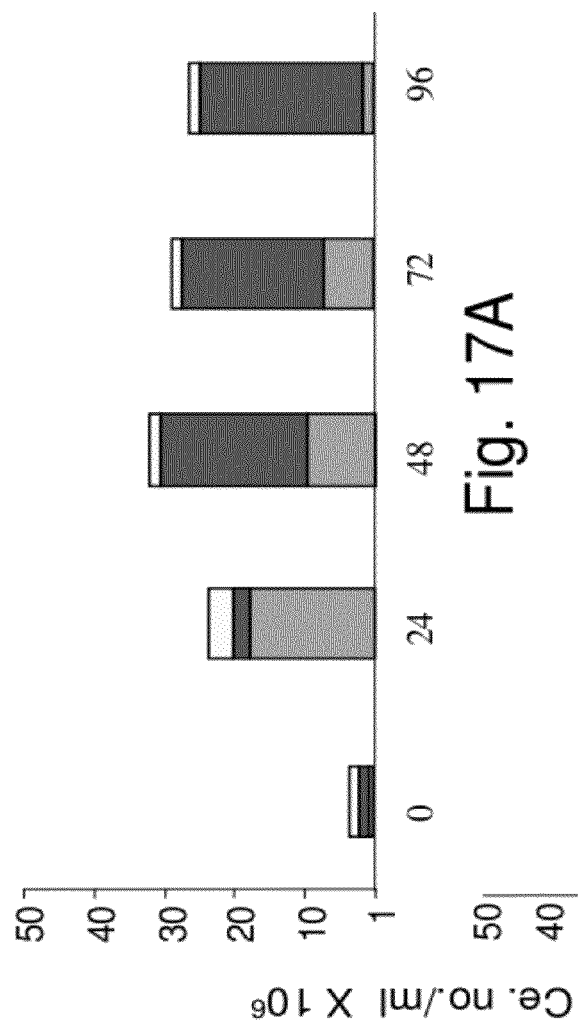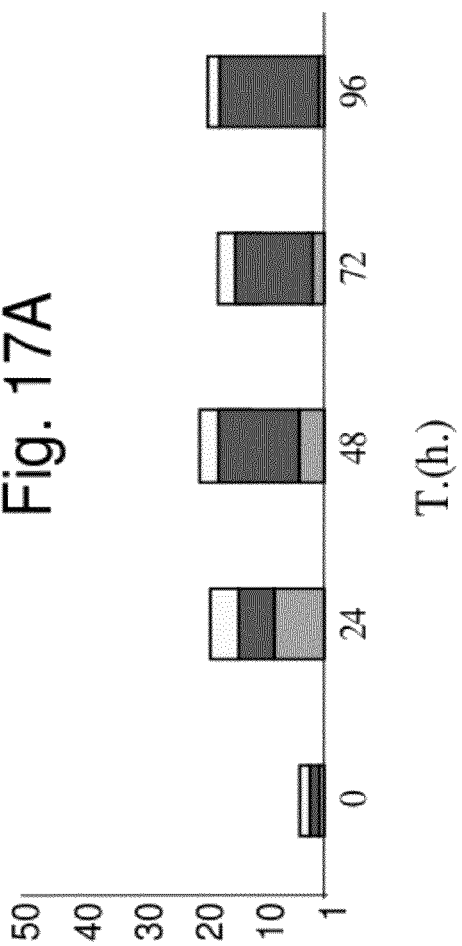

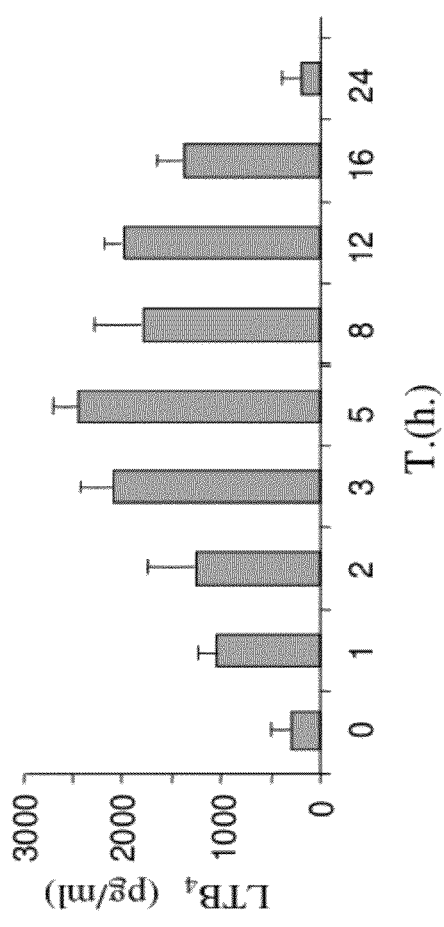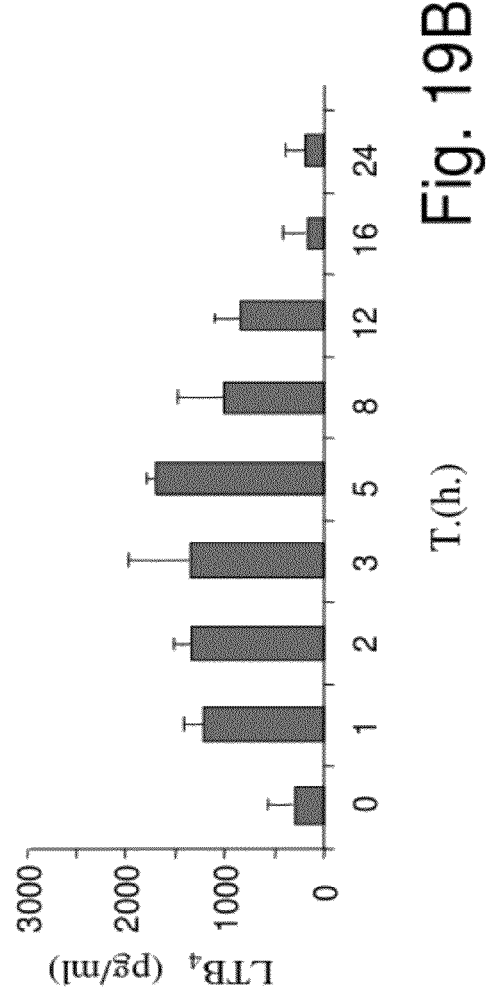

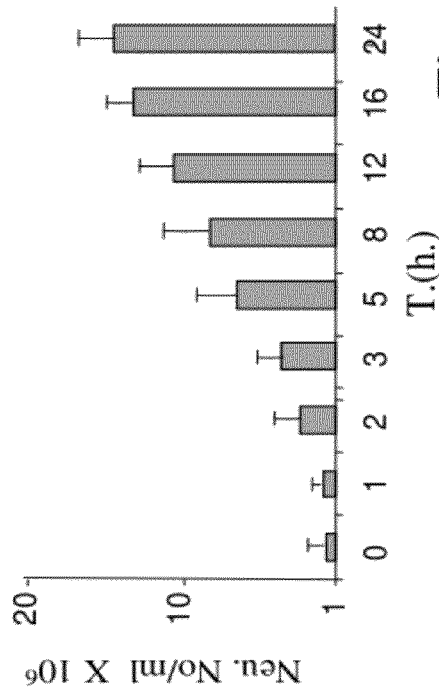
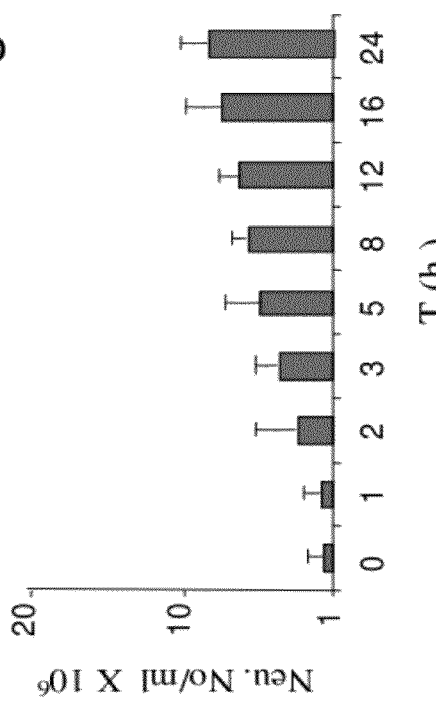

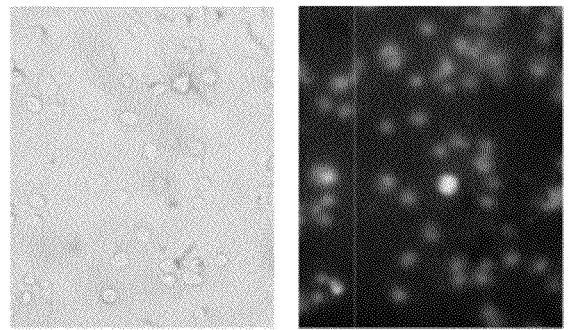
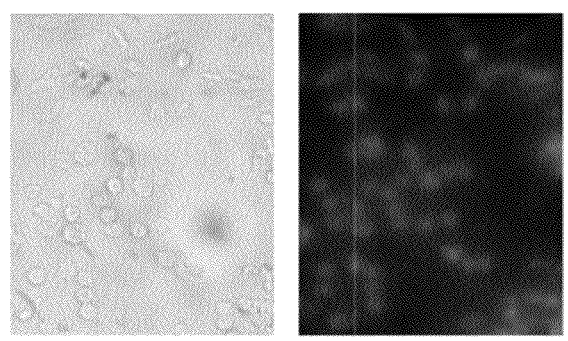
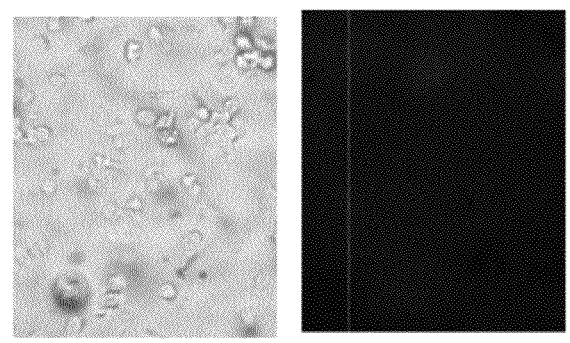
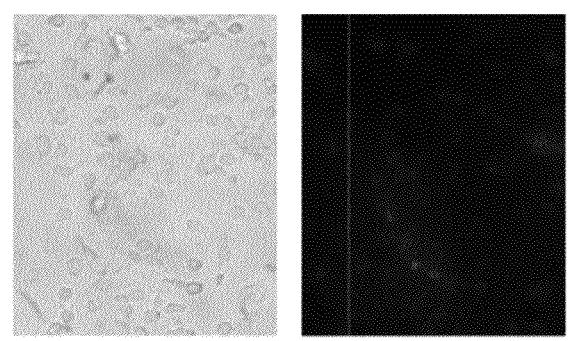
Fig. 21B  + as.
Fig. 21A

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 1
ttcaaaggtc tcattccaca                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Antisense Oligonucleotide
```

<400> SEQUENCE: 2
cactataatg tgctggtaag                                        20

<210> SEQ ID NO 3
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 3
caaaacattt tcctgattag g                                      21

<210> SEQ ID NO 4
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 4
cacagggttt atgtcattat                                        20

<210> SEQ ID NO 5
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 5
ccgtaaactt gtgggaatac                                        20

<210> SEQ ID NO 6
<211> LENGTH: 17
<212> TYPE: DNA
<213> ORGANISM: Artificial Sequence
<220> FEATURE:
<223> OTHER INFORMATION: Synthetic Antisense Oligonucleotide

<400> SEQUENCE: 6
gctgtcaggg gttgtag                                           17

<210> SEQ ID NO 7
<211> LENGTH: 2875
<212> TYPE: DNA
<213> ORGANISM: homo sapiens

<400> SEQUENCE: 7
gaattctccg gagctgaaaa aggatcctga ctgaaagcta gaggcattga ggagcctgaa      60
gattctcagg ttttaaagac gctagagtgc caaagaagac tttgaagtgt gaaaacattt     120
cctgtaattg aaaccaaaat gtcatttata gatccttacc agcacattat agtggagcac     180
cagtattccc acaagtttac ggtagtggtg ttacgtgcca ccaaagtgac aaaggggggcc   240 tttggtgaca tgcttgatac tccagatccc tatgtggaac tttttatctc tacaaccct      300 gacagcagga agagaacaag acatttcaat aatgacataa accctgtgtg gaatgagacc     360
tttgaattta ttttggatcc taatcaggaa aatgttttgg agattacgtt aatggatgcc     420
aattatgtca tggatgaaac tctagggaca gcaactttg ctgtatcttc tatgaaggtg     480
ggagaaaaga aagaagttcc ttttattttc aaccaagtca ctgaaatggt tctagaaatg     540

```
tctcttgaag tttgctcatg cccagaccta cgatttagta tggctctgtg tgatcaggag    600
aagactttca gacaacagag aaaagaacac ataagggaga gcatgaagaa actcttgggt    660
ccaaagaata gtgaaggatt gcattctgca cgtgatgtgc ctgtggtagc catattgggt    720
tcaggtgggg gtttccgagc catggtggga ttctctggtg tgatgaaggc attatacgaa    780
tcaggaattc tggattgtgc tacctacgtt gctggtcttt ctggctccac ctggtatatg    840
tcaaccttgt attctcaccc tgattttcca gagaaagggc cagaggagat taatgaagaa    900
ctaatgaaaa atgttagcca caatcccctt ttacttctca caccacagaa agttaaagga    960
tatgttgagt ctttatggaa gaagaaaagc tctggacaac tgtcacctt tactgacatc    1020 tttgggatgt taataggaga aacactaatt cataatagaa tgaatactac tctgagcagt    1080
ttgaaggaaa aagttaatac tgcacaatgc cctttacctc ttttcacctg tcttcatgtc    1140
aaacctgacg tttcagagct gatgtttgca gattgggttg aatttagtcc atacgaaatt    1200
ggcatggcta aatatggtac ttttatggct cccgacttat ttggaagcaa attttttatg    1260
ggaacagtcg ttaagaagta tgaagaaaac cccttgcatt tcttaatggg tgtctggggc    1320
agtgcctttt ccatattgtt caacagagtt ttgggcgttt ctggttcaca aagcagaggc    1380
tccacaatgg aggaagaatt agaaaatatt accacaaagc atattgtgag taatgatagc    1440
tcggacagtg atgatgaatc acacgaaccc aaaggcactg aaaatgaaga tgctggaagt    1500
gactatcaaa gtgataatca agcaagttgg attcatcgta tgataatggc cttggtgagt    1560
gattcagctt tattcaatac cagagaagga cgtgctggga aggtacacaa cttcatgctg    1620
ggcttgaatc tcaatacatc ttatccactg tctcctttga gtgactttgc cacacaggac    1680
tcctttgatg atgatgaact ggatgcagct gtagcagatc ctgatgaatt tgagcgaata    1740
tatgagcctc tggatgtcaa aagtaaaaag attcatgtag tggacagtgg gctcacattt    1800
aacctgccgt atcccttgat actgagacct cagagagggg ttgatctcat aatctccttt    1860 gactttctg caaggccaag tgactctagt cctccgttca aggaacttct acttgcagaa    1920
aagtgggcta aaatgaacaa gctccccttt ccaaagattg atccttatgt gtttgatcgg    1980
gaagggctga aggagtgcta tgtctttaaa cccaagaatc ctgatatgga aaagattgc    2040 ccaaccatca tccactttgt tctggccaac atcaacttca gaaagtacaa ggctccaggt    2100
gttccaaggg aaactgagga agagaaagaa atcgctgact tgatattttt tgatgaccca    2160
gaatcaccat tttcaacctt caattttcaa tatccaaatc aagcattcaa aagactacat    2220
gatcttatgc acttcaatac tctgaacaac attgatgtga taaagaagc catggttgaa    2280 agcattgaat atagaagaca gaatccatct cgttgctctg tttcccttag taatgttgag    2340
gcaagaagat ttttcaacaa ggagtttcta agtaaaccca agcatagtt catgtactgg    2400 aaatggcagc agtttctgat gctgaggcag tttgcaatcc catgacaact ggatttaaaa    2460
gtacagtaca gatagtcgta ctgatcatga gagactggct gatactcaaa gttgcagtta    2520
cttagctgca tgagaataat actattataa gttaggtgac aaatgatgtt gattatgtaa    2580
ggatatactt agctacattt tcagtcagta tgaacttcct gatacaaatg tagggatata    2640
tactgtattt ttaaacattt ctcaccaact ttcttatgtg tgttcttttt aaaaattttt    2700
tttcttttaa atatttaac agttcaatct caataagacc tcgcattatg tatgaatgtt    2760
attcactgac tagatttatt cataccatga gacaacacta tttttattta tatatgcata    2820
tatatacata catgaaataa atacatcaat ataaaaataa aaaaaaacgg aattc         2875
```

```
<210> SEQ ID NO 8
<211> LENGTH: 21
<212> TYPE: DNA
<213> ORGANISM: Artificial Sequence
<220> FEATURE:
<223> OTHER INFORMATION: Synthetic Antisense Oligonucleotide

<400> SEQUENCE: 8
gtaaggatct ataaatgaca t                                              21

<210> SEQ ID NO 9
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 9 cccctttgt cactttggtg                                                 20

<210> SEQ ID NO 10
<211> LENGTH: 18
<212> TYPE: DNA
<213> ORGANISM: Artificial Sequence
<220> FEATURE:
<223> OTHER INFORMATION: Synthetic Antisense Oligonucleotide

<400> SEQUENCE: 10
gcccaaaact ctgttgaa                                                  18

<210> SEQ ID NO 11
<211> LENGTH: 18
<212> TYPE: DNA
<213> ORGANISM: Artificial Sequence
<220> FEATURE:
<223> OTHER INFORMATION: Synthetic Antisense Oligonucleotide

<400> SEQUENCE: 11
ttgtgaacca gaaacgcc                                                  18

<210> SEQ ID NO 12
<211> LENGTH: 18
<212> TYPE: DNA
<213> ORGANISM: Artificial Sequence
<220> FEATURE:
<223> OTHER INFORMATION: Synthetic Antisense Oligonucleotide

<400> SEQUENCE: 12
gtgctggtaa ggatctat                                                  18
```

ANTISENSE OLIGONUCLEOTIDES AGAINST CPLA$_2$, COMPOSITIONS AND USES THEREOF

FIELD OF THE INVENTION

The present invention relates to the field of use of antisense oligonucleotides in the treatment of medical conditions. More specifically, the present invention describes novel antisense oligonucleotides for inhibition of phospholipase A$_2$ (PLA$_2$) and treatment of conditions associated with the activation of this molecule.

BACKGROUND OF THE INVENTION

All publications mentioned throughout this application are fully incorporated herein by reference, including all references cited therein.

Inflammation is the body's response to injury, infection or to molecules perceived by the immune system as foreign. Absent, excessive or uncontrolled inflammation results in a vast array of diseases such as asthma, arthritis and autoimmune diseases, adult respiratory distress syndrome (ARDS), cardiovascular inflammation and gastrointestinal inflammation. Numerous studies have demonstrated the participation of primed neutrophils, monocytes and macrophages in such inflammatory diseases. More recently, the role of superoxides release by microglia cells in the pathogenesis of neurodegenerative diseases such as Alzheimer's disease (AD), Parkinson's disease (PD) and amyotrophic lateral sclerosis (ALS) as well as brain ischemic and traumatic injury has also been documented.

The production of superoxides by the phagocyte NADPH oxidase and pro inflammatory lipid mediators by phospholipase A$_2$ are among the most important functions for host defense. However, during altered physiological states, superoxides and lipid mediators promote inflammatory reactions and participate in processes that lead to tissue injury and the pathophysiology of various inflammatory diseases. Nowadays non-steroidal anti-inflammatory drugs (NSAIDs) are one of the most widely prescribed drugs for the treatment of inflammatory conditions. However, they present unwanted side effects, the most common being ulceration and bleeding in the gastrointestinal tract. Moreover, these drugs reduce only the production of prostaglandins and do not affect the production of leukotrienes which have a pivotal role in the recruitment of neutrophils to the site of inflammation. Thus, the search for new anti-inflammatory drugs with fewer side effects continues. Numerous trials have been conducted with agents that block the inflammatory cascade, like corticosteroids, antiendotoxin antibodies, TNF antagonists, IL-1 receptor antagonists and other agents, without significant success.

The present inventor has developed a cell line, stable clones of PLB-985 cells lacking the expression of cytosolic phospholipase A$_2$ (cPLA$_2$), and demonstrated that cPLA$_2$, in addition to its known role in the production of pro-inflammatory lipid mediators, is essential for activation of the phagocyte NADPH oxidase complex after its assembly. The association between these two enzymes provides the molecular basis for activation of the assembled NADPH oxidase by arachidonic acid (AA) released by cPLA$_2$. [Dana, R. et al. (1998) *J. Biol. Chem.* 273:441-5; Lowenthal, A. and Levy, R. (1999) *J. Biol. Chem.* 274: 21603-10; Levy, R. et al. (2000) *Blood.* 95:660-5; Pessach, I. et al. (2001) *J. Biol. Chem.* 276:33495-503; Shmelzer, Z. et al. (2003) *J. Cell Biol.* 162:683-692; Tarsi-Tsuk, D. and Levy, R. (1990) J. Immunol.; 144:2665-2670; Dana, R. et al. (1994) *Biochem J.* 297:21'7-223; Hazan-Halevy, I. et al. (2000) *J. Biol. Chem.* 275:12416-12423]. Since cPLA$_2$ is required for oxidase activation, its inhibition should not only diminish the formation of inflammatory mediators, but should also regulate the uncontrolled accelerated release of oxygen radicals that participate in the pathogenesis of inflammatory diseases. Moreover, the inventor's studies have shown that during inflammation in vivo or inflammatory conditions in vitro, the level and activity of both cPLA$_2$ and NADPH oxidase enzymes are elevated, in neutrophils and monocytes [Levy, R. et al. (1994) *Biochim. Biophys. Acta* 1220:261-265; Shaked, G. et al. (1994) *J. Trauma* 37:22-29; Levy, R. et al. (2000) *Blood* 95:660-665; Levy, R. and Malech, H. (1991) *J. Immunol.* 147:3066-3071; Levy, R. et al. (1994) *Biochim. Biophys. Acta* 1220:253-260; Reizenberg, K. et al. (1997) *Eur. J. Clin. Invest.* 27:398-404]. Surprisingly, a recent report described that addition of cPLA$_2$ inhibitor pyrrolidine to neutrophils did not inhibit NADPH oxidase activity [Rubin, B. B. et al. (2005) *J. Biol. Chem.* 280:7519-29], however this effect might have been due to the methodology applied, which did not allow sufficient accumulation of the drug in the neutrophils (data not shown). Although methods of treating inflammatory conditions by inhibiting cPLA$_2$ have been described, they involved the use of substances like trifuoromethylketone (TFMK), causing dose-dependent attenuation of airway inflammation [US Patent Application No. 20020165119, USSN 062730], or indole compounds, which inhibited various forms of PLA$_2$ [U.S. Pat. No. 6,797, 708], but no inhibitor unique to cPLA$_2$ has been described for treatment of inflammation to date. Currently, potent cytosolic PLA$_2$ inhibitors are not available for clinical use in human or animals. All inhibitors against cPLA$_2$ so far were engineered to compete with the substrate. Since all types of PLA$_2$ cleave the fatty acid from the sn-2 position of phospholipids, they are also inhibited by the same inhibitors (although some times with lower efficiency). Although several compounds were described as specific inhibitors of cPLA$_2$, they were found to also inhibit other PLA$_2$ enzymes and vice versa. Because of the lack of specific inhibitor for each PLA$_2$ subtype, the antisense technology provides an effective approach to inhibit, a specific type of PLA$_2$. Indeed, the results presented herein suggest that a drug targeted directly to cPLA$_2$ will specifically inhibit cPLA$_2$ activity. Moreover it also results in the regulation of both cPLA$_2$ and NADPH oxidase to produce pro-inflammatory mediators and superoxides.

Antisense oligonucleotides targeted against the cPLA$_2$ mRNA sequence have been reported in the past as capable of inhibiting cPLA$_2$ transcript expression [U.S. Pat. No. 6,008, 344]. However, these oligonucleotides did not demonstrate inhibition of cPLA$_2$ protein expression, and were introduced into cells in the presence of lipofectin.

In addition, three other antisense oligonucleotides targeted to cPLA$_2$ have been described; P1 (Table 1, SEQ. ID. No. 8) [Roshak, A. (1994) *J. Biol. Chem.* 269(42): 25999-26005; Muthalif, M. M. et al. (1996) *J. Biol. Chem.* 271(47): 30149-30157; Marshall, L. (1997) *J. Biol. Chem.* 272(2): 759-765; Anderson, K. M. et al. (1997) *J. Biol. Chem.* 272(48): 30504-30511]; P2 (Table 1, SEQ. ID. No. 9) [Li, Q. and Cathcart, M. K. (1997) *J. Biol. Chem.* 272(4): 2404-2411; Zhao, X. et al. (2002) *J. Biol. Chem.* 277(28): 25385-25392]; and P3 (5'-GTGCTGGTAAGGATCTAT-3'; SEQ. ID. No. 12) [Locati, M. (1996) *J. Biol. Chem.* 271(11): 6010-6016], mainly evaluating the effect of inhibiting cPLA$_2$ in smooth muscle cells and human monocytes function. P1 was used together with lipofectin. P1 and P2, with phosphorothioate modifications in all bases, had a significant effect only when used at 5 μM, which the present inventor found to be toxic to the cells. P3 was used at 10 µM (or even higher concentration, 10 times higher than what was used by the present inventor).

Thus, it is an object of the present invention to provide novel antisense oligonucleotides against the $cPLA_2$ mRNA, and their use in the inhibition of $cPLA_2$ expression and superoxide production, in order to inhibit pro-inflammatory processes. Consequently, the antisense oligonucleotides claimed in the present invention are also sought as anti-inflammatory agents.

Other uses and objects of the invention will become clear as the description proceeds.

SUMMARY OF THE INVENTION

In a first aspect, the present invention provides antisense oligonucleotides directed against the open reading frame (ORF) of the cytosolic phospholipase $A_2$ ($cPLA_2$) mRNA sequence, and functional analogs, derivatives or fragments thereof, wherein the complementarity of said antisense oligonucleotide is within the region between nucleotides 145 to 400 of said ORF, and wherein said antisense oligonucleotide is capable of inhibiting the expression of the $cPLA_2$ protein.

In one embodiment, the antisense oligonucleotide of the invention is from 15 up to 30 nucleotides long, preferably 17 to 21 nucleotides long.

Said antisense oligonucleotide directed against the 5 region of the open reading frame of the $cPLA_2$, mRNA sequence has the sequence as denoted by any one of SEQ. ID. No. 1, SEQ. ID. No. 2, SEQ. ID. No. 3, SEQ. ID. No. 4, SEQ. ID. No. 5, and SEQ. ID. No. 6, and as detailed in Table 1.

The antisense oligonucleotides of the invention can be chemically modified, so as to possess improved endonuclease resistance.

Thus, in another embodiment of the antisense oligonucleotide of the invention, a phosphorothioate modification may be present on the first three and/or the last three nucleotides of said oligonucleotides. In addition, another phosphorothioate modification may be found on the tenth nucleotide of said oligonucleotide, as for example in the oligonucleotides denoted by SEQ. ID. Nos. 4 and 5.

In a further embodiment of the antisense oligonucleotide of the invention, further modifications, like 2-O-methylation, may be found in the first three and/or the last three nucleotides of said oligonucleotide.

As a result of the properties presented in the present study, the antisense oligonucleotide may be used as an inhibitor of inflammation processes related to $cPLA_2$ expression.

Therefore, the antisense oligonucleotide of the invention is for use in the treatment and/or prevention of any one of rheumatoid arthritis, adult respiratory distress syndrome (ARDS), asthma, rhinitis, idiopathic pulmonary fibrosis, peritonitis, cardiovascular inflammation, myocardial ischemia, reperfusion injury, atherosclerosis, sepsis, trauma, diabetes type retinopathy, psoriasis, gastrointestinal inflammation, cirrhosis and inflammatory bowel disease, and neurodegenerative diseases, such as for example Alzheimer's disease (AD), Parkinson's disease (PD), amyotrophic lateral sclerosis (ALS), as well as brain ischemic and traumatic injury, i.e. in all diseases where oxidative stress has a significant role in its pathogenesis, and in which there is accelerated release of eicosanoids and superoxides by reactive microglia.

Thus, the antisense oligonucleotide of the invention may be used for inhibiting superoxide production and release. In particular, said inhibition is effectuated in neutrophils, monocytes and macrophages, preferably in neutrophils.

Optionally the antisense oligonucleotide of the invention may be labeled with one of fluorescent, radioactive, metal particle, and any suitable labeling means.

In a second aspect, the present invention relates to a pharmaceutical composition comprising as active agent at least one antisense oligonucleotide as defined in the invention, or functional analogs, derivatives or fragments thereof.

Thus, the antisense oligonucleotide of the invention is generally provided in the form of pharmaceutical compositions. Said compositions are for use by injection, topical administration, or oral uptake.

Alternatively, the pharmaceutical composition of the invention may comprise as active agent a combination of at least two antisense oligonucleotides as defined in the invention, or functional analogs, derivatives or fragments thereof. Preferably, said combination comprises the following oligonucleotides: SEQ. ID. No. 1, together with SEQ. ID. No. 3, or SEQ. ID. No. 1 together with SEQ. ID. No. 2, or SEQ. ID. No. 1 together with SEQ. ID. No. 6, or SEQ. ID. No. 1 together with SEQ. ID. No. 2 and SEQ. ID. No. 3, or SEQ. ID. No. 4 together with SEQ. ID. No. 6, or SEQ. ID. No. 2 together with SEQ. ID. No. 6, or SEQ. ID. No. 2 together with SEQ. ID. No. 3, or SEQ. ID. No. 3 together with SEQ. ID. No. 6.

The pharmaceutical composition of the invention is intended for medical use.

In one embodiment, the pharmaceutical composition of the invention is intended for the treatment of inflammation processes related to $cPLA_2$ expression and/or free radical release by phagocyte NADPH oxidase.

In another embodiment, the pharmaceutical composition of the invention is intended for the treatment of inflammatory conditions, wherein said inflammatory conditions may be any one of rheumatoid arthritis, ARDS, asthma, rhinitis, idiopathic pulmonary fibrosis, peritonitis, cardiovascular inflammation, myocardial ischemia, reperfusion injury, atherosclerosis, sepsis, trauma, diabetes type II, retinopathy, psoriasis, gastrointestinal inflammation, cirrhosis and inflammatory bowel disease, CNS-related diseases such as the neurodegenerative diseases AD, PD, ALS, as well as brain ischemic and traumatic injury, i.e. in all diseases where oxidative stress has a significant role in its pathogenesis, and in which there is accelerated release of eicosanoids and superoxides by reactive microglia.

In a further embodiment, the pharmaceutical composition of the invention is intended for the treatment of conditions related to Aβ plaque accumulation. Said conditions are generally CNS-related diseases, particularly the neurodegenerative diseases Alzheimer's, Parkinson's and ALS, or brain ischemic and traumatic head injury.

The pharmaceutical composition of the invention may optionally further comprise buffers, additives, stabilizers, diluents and/or excipients.

In another aspect, the present invention provides the use of the antisense oligonucleotide as defined in the invention, for the preparation of a pharmaceutical composition for the treatment and/or prevention of inflammatory conditions, wherein said inflammatory conditions may be any one of rheumatoid arthritis, ARDS, asthma, rhinitis, idiopathic pulmonary fibrosis, peritonitis, cardiovascular inflammation, myocardial ischemia, reperfusion injury, atherosclerosis, sepsis, trauma, diabetes type II, retinopathy, psoriasis, gastrointestinal inflammation cirrhosis and inflammatory bowel disease, neurodegenerative diseases such as AD, PD and ALS, as well as brain ischemic and traumatic injury, i.e. in all diseases where oxidative stress has a significant role in its pathogenesis, and in which there is accelerated release of eicosanoids and superoxides by reactive microglia.

In a further aspect, the present invention provides the use of an antisense oligonucleotide as defined in the invention for the treatment of conditions associated with cPLA$_2$ activation.

In addition, the present invention presents the use of an antisense oligonucleotide as defined in the invention, for the treatment and/or prevention of conditions related to Aβ plaque accumulation. Generally said conditions are CNS-related diseases selected from the group consisting of Alzheimer's disease, Parkinson's disease, ALS, brain ischemic injury and traumatic head injury.

In an even further aspect, the present invention presents a method of treatment of conditions associated with cPLA$_2$ activation, comprising administering a therapeutically effective amount of at least one antisense oligonucleotide as defined in the invention, or compositions comprising thereof, to a subject in need.

Therefore, in yet another aspect, the present invention provides a method of treatment of inflammatory conditions, wherein said inflammatory conditions are any one of rheumatoid arthritis, ARDS, asthma, rhinitis, idiopathic pulmonary fibrosis, peritonitis, cardiovascular inflammation, myocardial ischemia, reperfusion injury, atherosclerosis, sepsis, trauma, diabetes type retinopathy, psoriasis, gastrointestinal inflammation, cirrhosis and inflammatory bowel disease, neurodegenerative diseases such as AD, PD and ALS, as well as brain ischemic and traumatic injury, i.e. in all diseases where oxidative stress has a significant role in its pathogenesis, and in which there is accelerated release of eicosanoids and superoxides by reactive microglia, comprising administering a therapeutically effective amount of at least one antisense oligonucleotide as defined in the invention, or compositions comprising thereof, to a subject in need.

In one more aspect, the present invention provides a method of treatment of conditions related to Aβ plaque accumulation, comprising administering a therapeutically effective amount of at least one antisense oligonucleotide as defined in the invention, or compositions comprising thereof, to a subject in need. Said conditions are generally neurodegenerative diseases, particularly Alzheimer's and Parkinson's disease.

Finally, the present invention provides all in vivo, ex vivo, in vitro method of inhibiting cPLA$_2$ expression and/or activity, comprising contacting cells, preferably phagocytes, i.e. neutrophils, monocytes, macrophages and/or microglia, with the antisense oligonucleotide described in the invention or with compositions comprising thereof, for a suitable amount of time. These antisense oligonucleotides inhibited the cPLA2 activity in fibroblasts, neuronal cells and endothelial cells, but with lower efficiency compared to phagocytes, probably due to lower permeability of the former cells to the antisense oligonucleotides (data not shown).

BRIEF DESCRIPTION OF THE FIGURES

The file of this patent contains at least one drawing executed in color photograph. Copies of this patent with color photograph(s) will be provided by the Patent and Trademark Office upon request and payment of necessary fee.

FIG. 1: cDNA Sequence of cPLA2 (SEQ. ID. No. 7), with Position of Antisense Oligonucleotides C2, C3, C4, C8, C9 and C10 Highlighted.

C2 encompasses nucleotides 347-366; C3 encompasses nucleotides 155-174; C4 encompasses nucleotides 379-399; C8 encompasses nucleotides 330-346; C9 encompasses nucleotides 183-202; and C10 encompasses nucleotides 290-306.

Figure 2A:
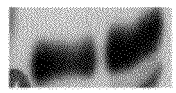

FIG. 2: Comparison Between Two Anti-cPLA$_2$ Antibodies (Ab):

FIG. 2A: Levy's Ab [Hazan et al. (1997) id ibid.]

Figure 2B:

FIG. 2B: commercial antibodies.

Dil.=dilution.

Figure 3A:
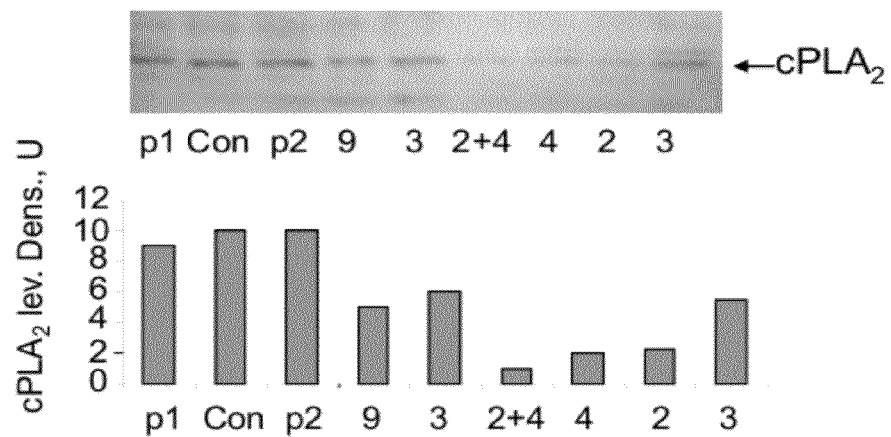
Figure 3B:
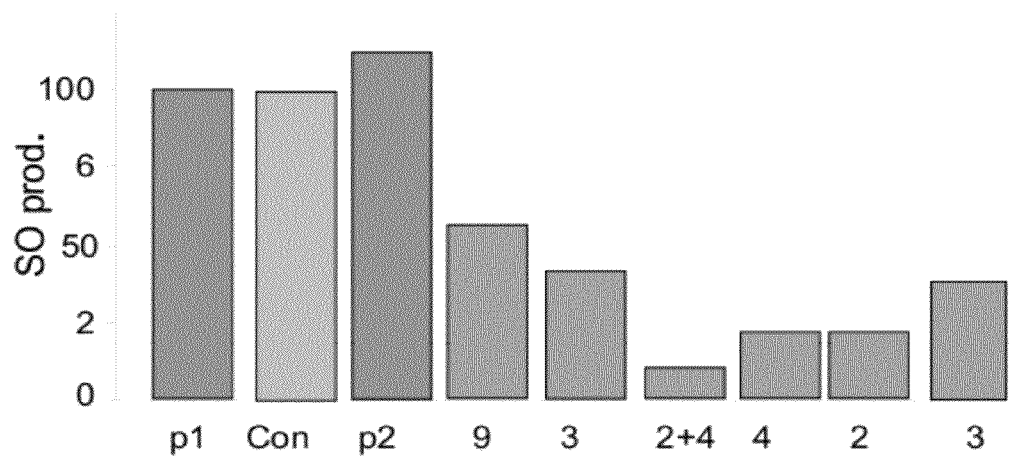

FIGS. 3A-3B: Effect of cPLA$_2$ Antisense PPS Oligonucleotides on cPLA$_2$ Expression and Superoxide Production in Human Peripheral Blood Monocytes.

FIG. 3A: Western blot analysis showing inhibition of cPLA$_2$ expression detected by anti-cPLA$_2$ antibodies after treatment with antisense PPS oligonucleotides C2, C3, C4, C9, and the combination of C2+C4 (2+4), in comparison to control and to the antisense P1 [Roshak, A et al. (1994) id ibid.; Marshall, L. et al. (1997) id ibid.; Muthalif, M. M. et al. (1996) id ibid.; Anderson, K. M. et al. (1997) id ibid.] and P2 [Li, Q. and Cathcart, M. K. (1997) id ibid.]. The level of cPLA$_2$ in the different treatment was quantified by densitometry and is presented below the Western blot analysis. Lev.=levels; dens.=densitometry.

FIG. 3B: Histogram showing inhibition of superoxide production (SO prod.) by cPLA$_2$ antisense PPS oligonucleotides C2, C3, C4, C9, and the combination of C2+C4 (2+4), in comparison to control and to the antisense P1 [Muthalif, M. M. et al. (1996) id ibid.; Anderson, K. M. et al. (1997) at ibid.] and P2 [Li, Q. and Cathcart, M. K. (1997) id ibid.].

It is important to note the higher efficiency of the antisense PPS oligonucleotides of the invention (denoted as 2, 3, 4 and 9) versus the antisense oligonucleotides P1 and P2 described previously.

Figure 4A:
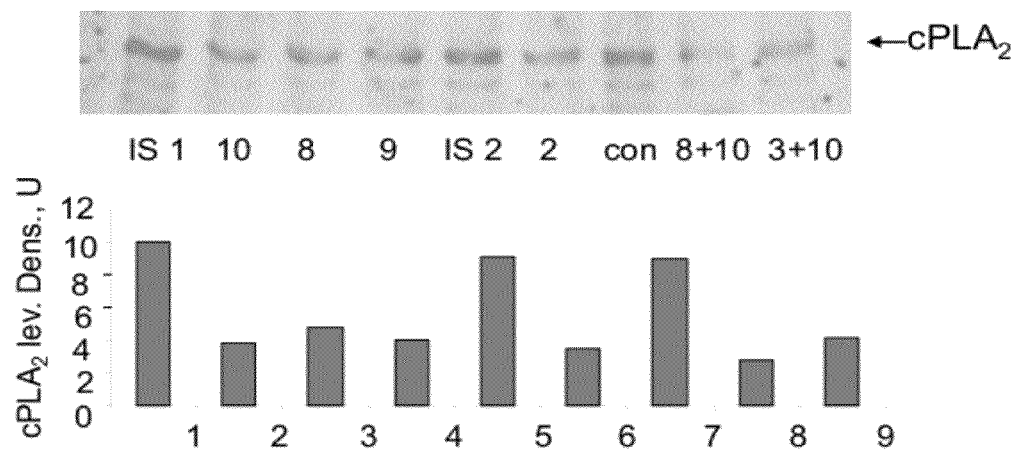
Figure 4B:
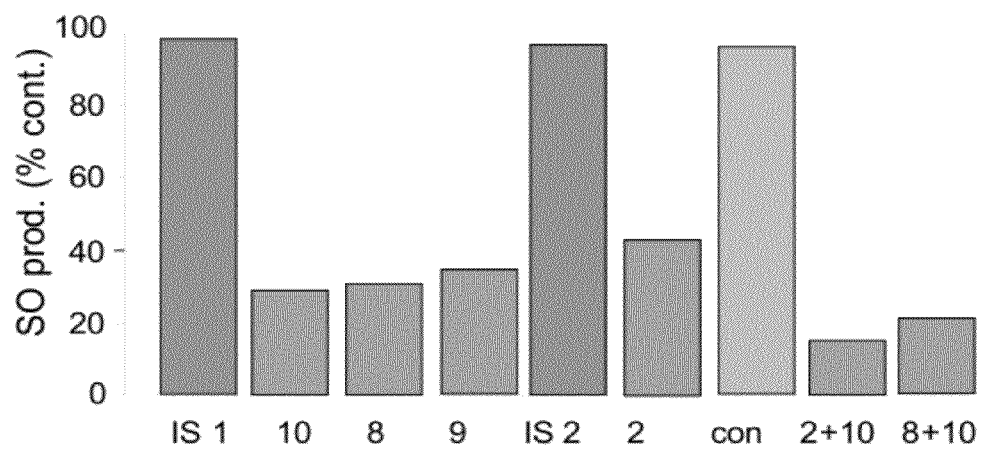

FIG. 4A-4B: Effect of cPLA$_2$, Antisense PPS Oligonucleotides on cPLA$_2$ Expression and Superoxide Production in Peripheral Blood Human Monocytes.

FIG. 4A: Western blot analysis showing inhibition of cPLA$_2$ expression detected by anti-cPLA$_2$ antibodies after treatment with antisense partially phosphorothioated (PPS) oligonucleotides C2, C8, C9, C10 and the combinations C3+C10 and C8+C10, in comparison to control and to the oligonucleotides IS1 and IS2 [U.S. Pat. No. 6,008,344]. The level of cPLA$_2$ in the different treatment was quantified by densitometry and is presented below the Western blot analysis. Lev.=levels; dens.=densitometry.

FIG. 4B: Histogram showing inhibition of superoxide production (SO prod.) by cPLA$_2$ antisense PPS oligonucleotides C2, C8, C9, C10 and the combinations C3+C10 and C8+C10, in comparison to control (cont.) and to the oligonucleotides IS1 and IS2 [U.S. Pat. No. 6,008,344].

It is important to note the higher efficiency of the antisense oligonucleotides of the invention (denoted as 2, 8, 9, and 10 in the Figure) versus the antisense oligonucleotides described in U.S. Pat. No. 6,008,344 (IS1 and IS2).

Figure 5A:
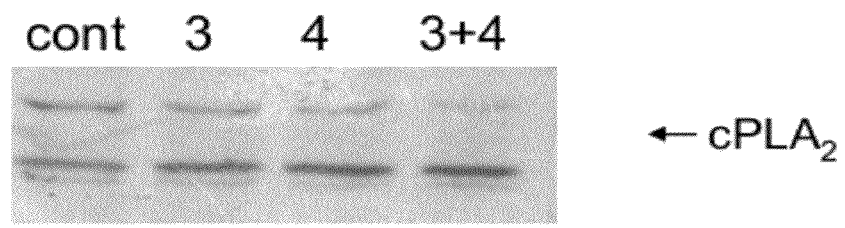
Figure 5B:
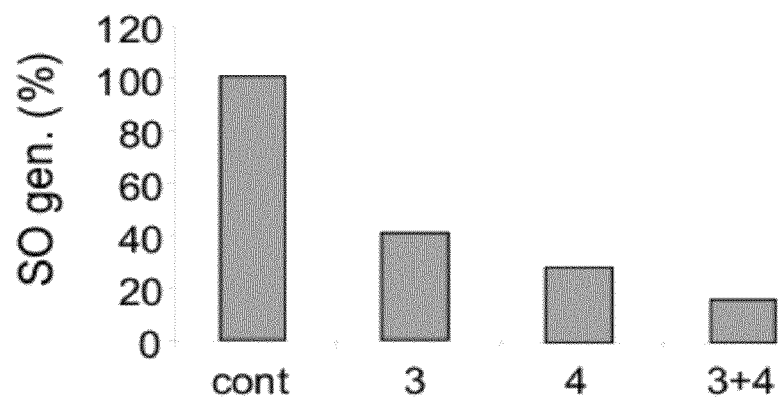
Figure 5C:
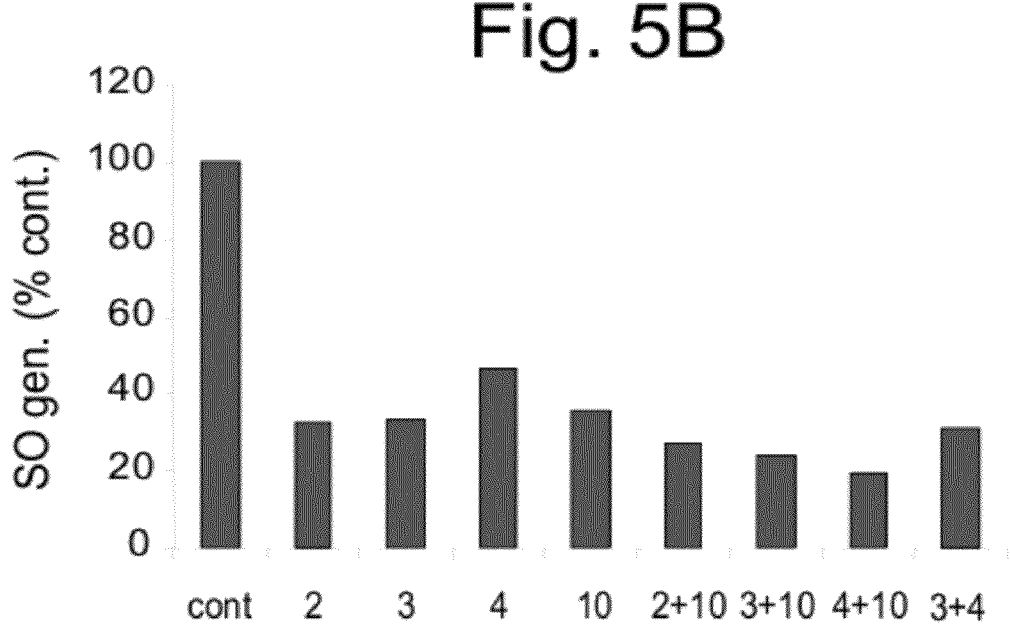

FIGS. 5A-5C: Effect of cPLA$_2$ Antisense PPS Oligonucleotides on cPLA$_2$ Expression and Superoxide Production in Peritoneal Murine Macrophages.

FIG. 5A: Western blot analysis showing inhibition of cPLA$_2$ expression detected by anti-cPLA$_2$ antibodies after treatment with antisense PPS oligonucleotides C3 and C4 and the combination C3+C4.

FIG. 5B: Histogram showing inhibition of superoxide production by cPLA$_2$ antisense PPS oligonucleotides C3 and C4 and the combination C3+C4.

FIG. 5C: Histogram showing inhibition of superoxide production by cPLA$_2$ antisense PPS oligonucleotides C2, C3, C4, C10 and the combinations C2+C10, C3+C10, C4+C10 and C3+C4.

Abbreviations: cont., control; SO gen., superoxide generation.

Figure 6:
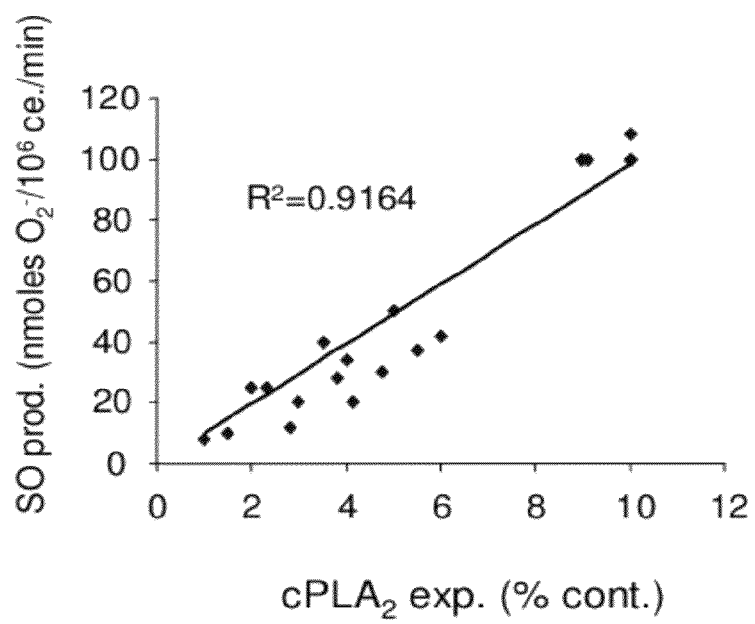

FIG. 6: Correlation Between Inhibition of $cPLA_2$ Expression (Exp.) and Superoxide Production (SO Prod.) Following Treatment with $cPLA_2$ Antisense PPS Oligonucleotides. Cont.=Control.

Figure 7A:
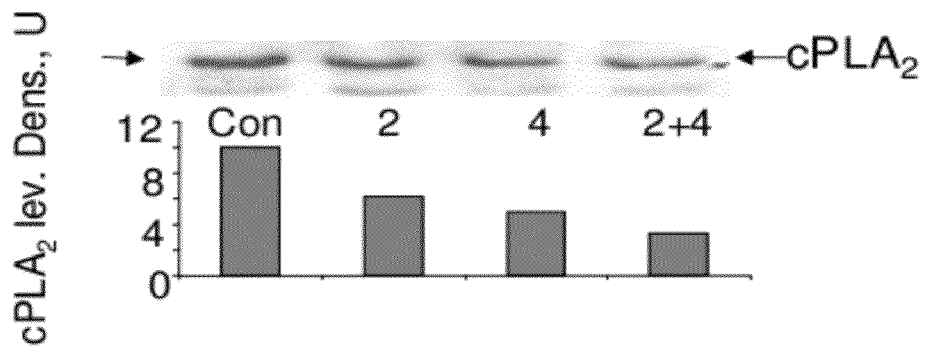
Figure 7B:
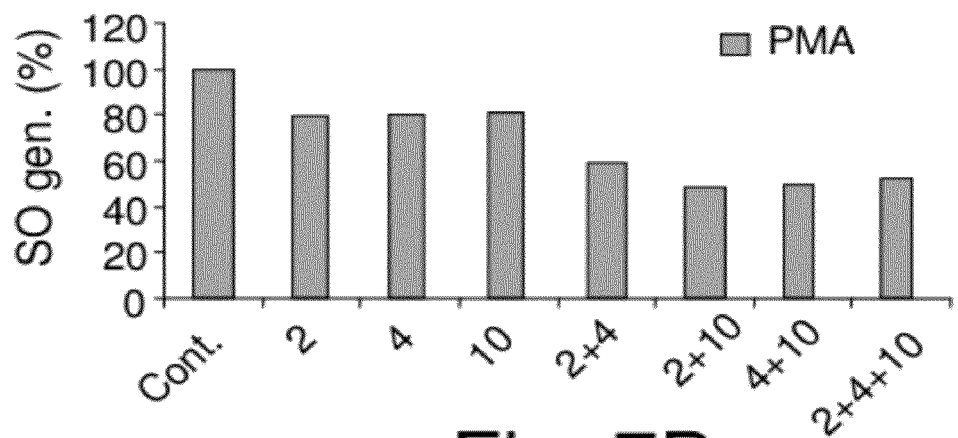
Figure 7C:
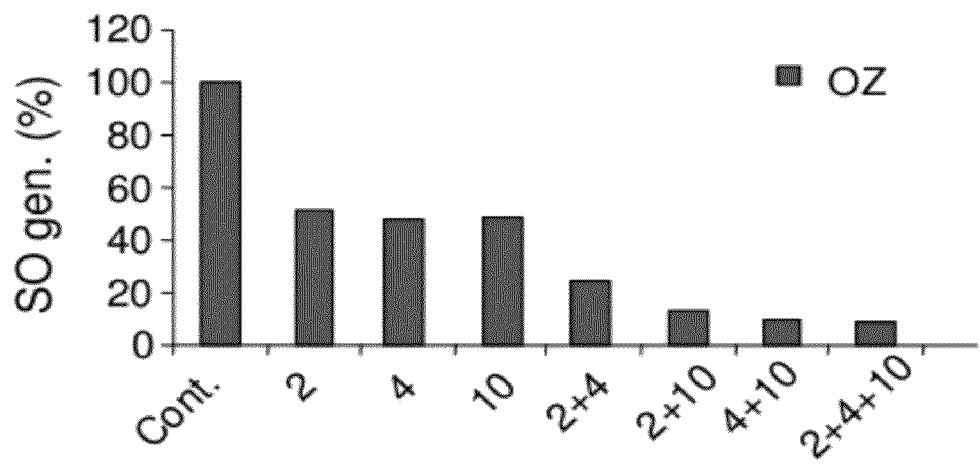

FIGS. 7A-7C: Effect of $cPLA_2$ Antisense PPS Oligonucleotides on $cPLA_2$ Expression and Superoxide Production in Peripheral Blood Human Neutrophils.

FIG. 7A: Western blot analysis showing inhibition of $cPLA_2$ expression detected by anti-$cPLA_2$ antibodies after treatment with antisense PPS oligonucleotides C2 or C4 and the combination C2+C4. The level of $cPLA_2$ in the different treatment was quantified by densitometry and is presented below the Western blot analysis.

FIG. 7B: Histogram showing inhibition of superoxide production by $cPLA_2$ antisense oligonucleotides C2, C4 or C10 and the combinations C2+C4, C2+C10, C4+C10, C2+C4+C10 following PMA treatment.

FIG. 7C: Histogram showing inhibition of superoxide production by $cPLA_2$ antisense oligonucleotides C2, C4 or C10 and the combinations C2+C4, C2+C10, C4+C10, C2+C4+C10 following OZ treatment.

Abbreviations: Lev., levels; dens., densitometry; cont., control; SO gen., superoxide generation.

FIG. 8A-F: Inhibition of Superoxide Production Stimulated by Physiologic Agonists Following $cPLA_2$ Antisense PPS Oligonucleotides Treatment in Neutrophils and Macrophages.

Figure 8A:
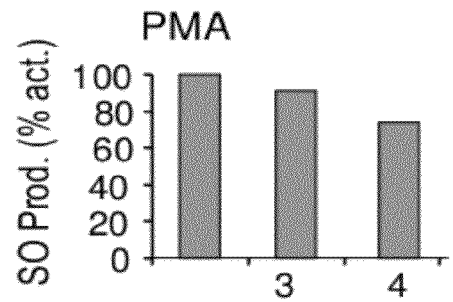

FIG. 8A: Histogram Showing Inhibition of Superoxide Production in PMA-Stimulated Neutrophils Following 6 Hours of Incubation with the $cPLA_2$ Antisense PPS Oligonucleotides C3 or C4.

Figure 8D:
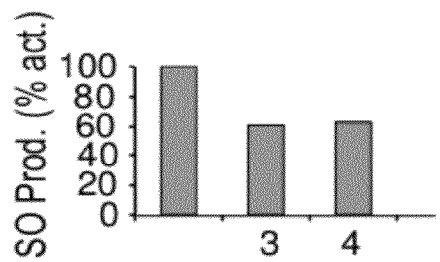
Figure 8B:
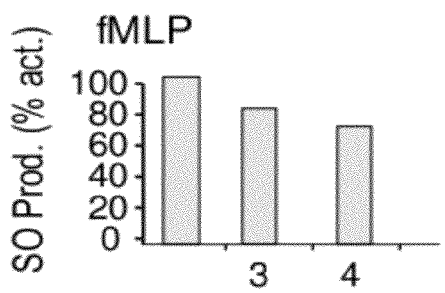

FIG. 8B: Histogram showing inhibition of superoxide production in fMLP-stimulated neutrophils following 4 hours of incubation with the $cPLA_2$ antisense PPS oligonucleotides C3 or C4.

Figure 8E:
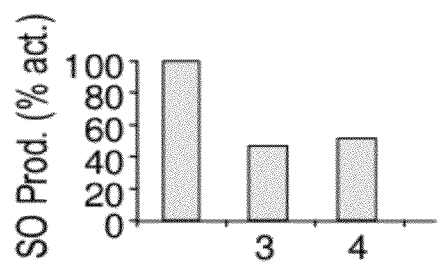
Figure 8C:
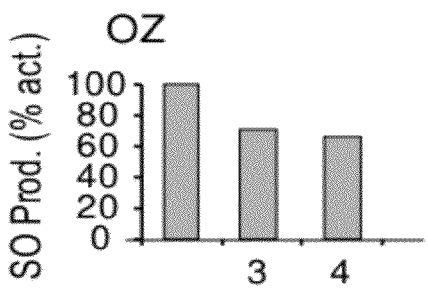

FIG. 8C: Histogram showing inhibition of superoxide production in OZ-stimulated neutrophils following 4 hours of incubation with the $cPLA_2$ antisense PPS oligonucleotides C3 or C4.

FIG. 8D: Histogram showing inhibition of superoxide production in PMA-stimulated monocytes following 16 hours of incubation with the $cPLA_2$ antisense PPS oligonucleotides C3 or C4.

FIG. 8E: Histogram showing inhibition of superoxide production in $cPLA_2$ stimulated monocytes following 16 hours of incubation with the $cPLA_2$ antisense PPS oligonucleotides C3 or C4.

Figure 8F:
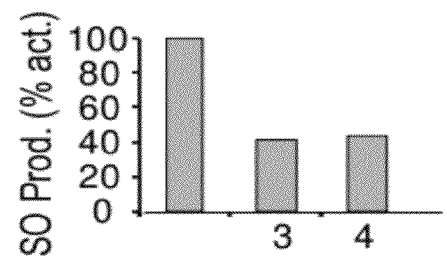

FIG. 8F: Histogram showing inhibition of superoxide production in OZ-stimulated monocytes following 1.6 hours of incubation with the $cPLA_2$ antisense PPS oligonucleotides C3 or C4.

Abbreviations: SO prod., superoxide production; Act., activity.

FIGS. 9A-9D: Inhibition of Stimulated Superoxide Production in Rat Microglia by $cPLA_2$ Antisense PPS Oligonucleotides.

Figure 9A:
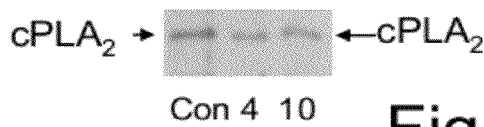

FIG. 9A: Western blot analysis showing inhibition of $cPLA_2$ expression detected by anti-$cPLA_2$ antibodies after treatment with antisense PPS oligonucleotides C2 or C4.

Figure 9B:
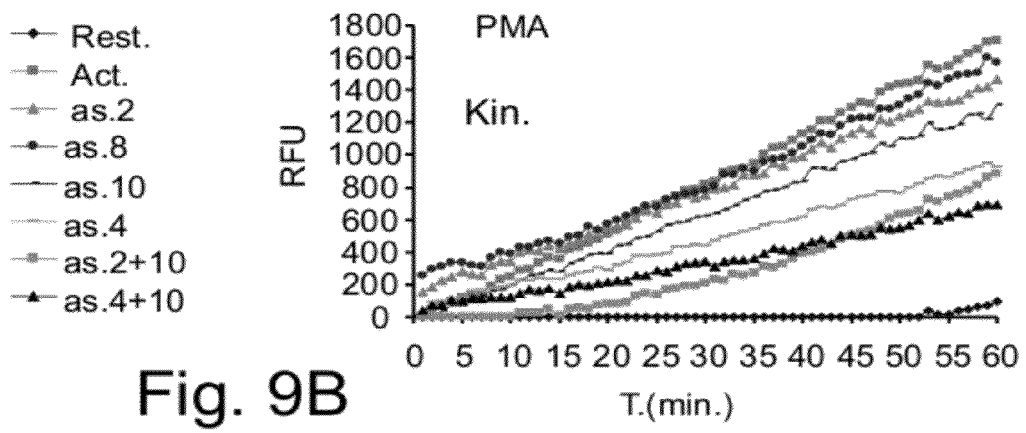

FIG. 9B: Graph demonstrating the kinetics of the inhibition of superoxide production in PMA-activated rat microglia cells following treatment with the $cPLA_2$ antisense oligonucleotides C2, C4, C8 or C10, and the combinations C2+C10 or C4+C10.

Figure 9C:
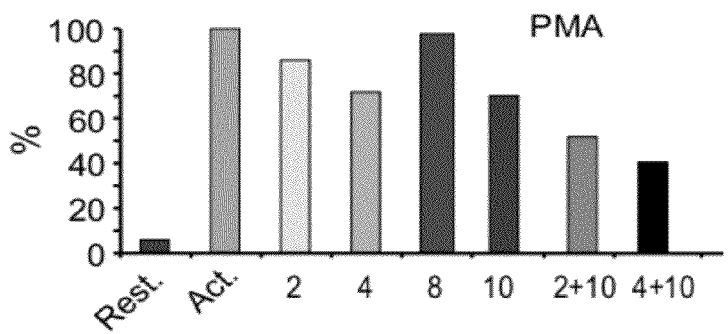

FIG. 9C: Histogram showing the effect of $cPLA_2$ antisense PPS oligonucleotides (C2, C4, C8 and C10, and the combinations C2+C10 and C4+C10) on superoxide production in rat microglia cells following PMA stimulation.

Figure 9D:
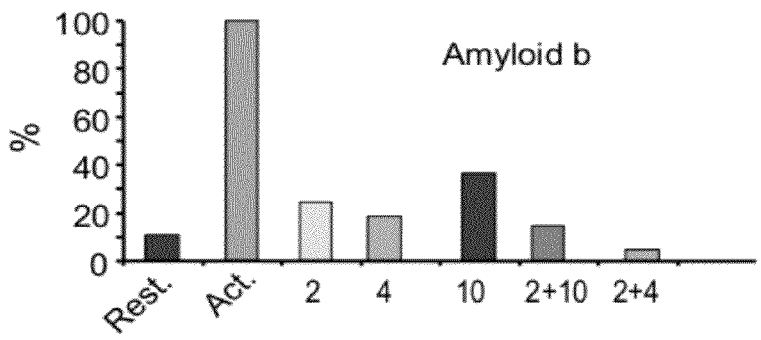

FIG. 9D: Histogram showing the effect of $cPLA_2$ antisense PPS oligonucleotides (C2, C4, and C10, and the combinations C2+C10 and C2+C4) on superoxide production in rat microglia cells following Amyloid β stimulation.

Abbreviations: rest., resting; act, activated; as, antisense; kin., kinetics; T., time, min., minutes.

FIGS. 10A-10C: Animal Model of Collagen-Induced Arthritis (CIA)

FIG. 10A: A picture of exacerbated CIA in experimental compared to control (cont.) mice.

FIG. 10B: Histological assessment of representative section of joint histopathology on whole paws of CIA mice compared to control (cont.) (×100).

FIG. 10C: Infiltration of inflammatory cells (×400) in CIA mice.

FIGS. 11A-11B: Treatment with a Combination of 3 $cPLA_2$ Antisense PPS Oligonucleotides ("Cocktail") Caused Remission of Arthritis.

FIG. 11A: Photograph of swollen limb of CIA mouse (top, art=arthritis) and limb CIA mouse post-treatment with the cocktail (bottom, as=antisense treatment). Both photographs were taken at same magnification and same distance from the animal.

FIG. 11B: Reduction in disease severity score (dis. sev. sc.), in serum (ser.) IL-6 and in serum TNFα after i.v. treatment with the cocktail (mean±SEM, from 5 mice in each group).

FIGS. 12A-12B: Number and Composition of Peritoneal Cell Population after Induction of Sterile Peritonitis.

FIG. 12A: Changes in peritoneal cell count in sterile peritonitis mice (mean±SEM, from 6 mice in each group).

FIG. 12B: Changes in the composition of the peritoneal cell population in sterile peritonitis mice.

Abbreviations: ce. no., cell number; T., time; h. hours; neu, neutrophils; mac, macrophages; lymp, lymphocytes.

FIGS. 13A-13B: $LTB_4$ Levels after Induction of Sterile Peritonitis.

FIG. 13A: $LTB_4$ levels in the serum (ser.).

FIG. 13B: $LTB_4$ levels in the peritoneal cavity (per. cav.). Mean±SEM from 5 mice in each group. T., time; h, hours.

Figure 14A:
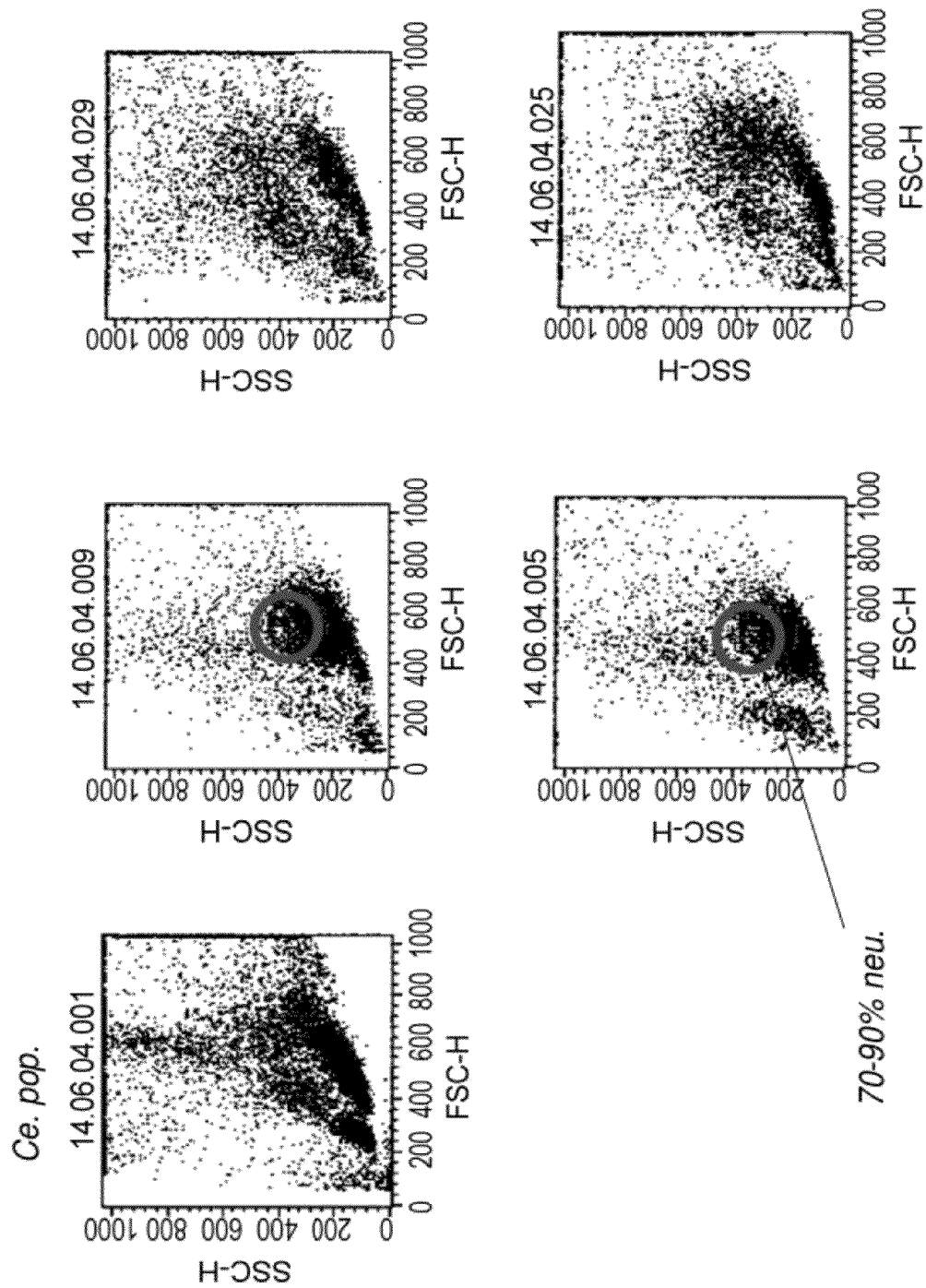

FIGS. 14A-14C: The Effect of Antisense PPS Oligonucleotide Cocktail Treatment on Peritoneal Cell Population and Activity after 24 Hours of Induction.

FIG. 14A: FACS anal of cell population (ce. pop.) composition. Neu=neutropils.

FIG. 14B: Graph demonstrating cell count (ce. co.).

FIG. 14C: Superoxide production (SO prod.) by stimulated peritoneal cells of control healthy mice (H), of sterile peritonitis mice (P) and of sterile peritonitis mice after 24 h of cocktail i.v. injection (P+AS).

FIGS. 15A-15B: $cPLA_2$ Antisense PPS Oligonucleotide Cocktail Treatment Decreased Neutrophils Number and Superoxide Production in Inflammation Site 24 Hours after Peritonitis Induction.

FIG. 15A: Graph demonstrating percentage of neutrophils (neu) with and without antisense treatment.

FIG. 15B: Graph presenting stimulated superoxide production (SO prod.) by PMA of peritoneal cells isolated from sterile peritonitis mice without and with antisense treatment.

Figure 16:
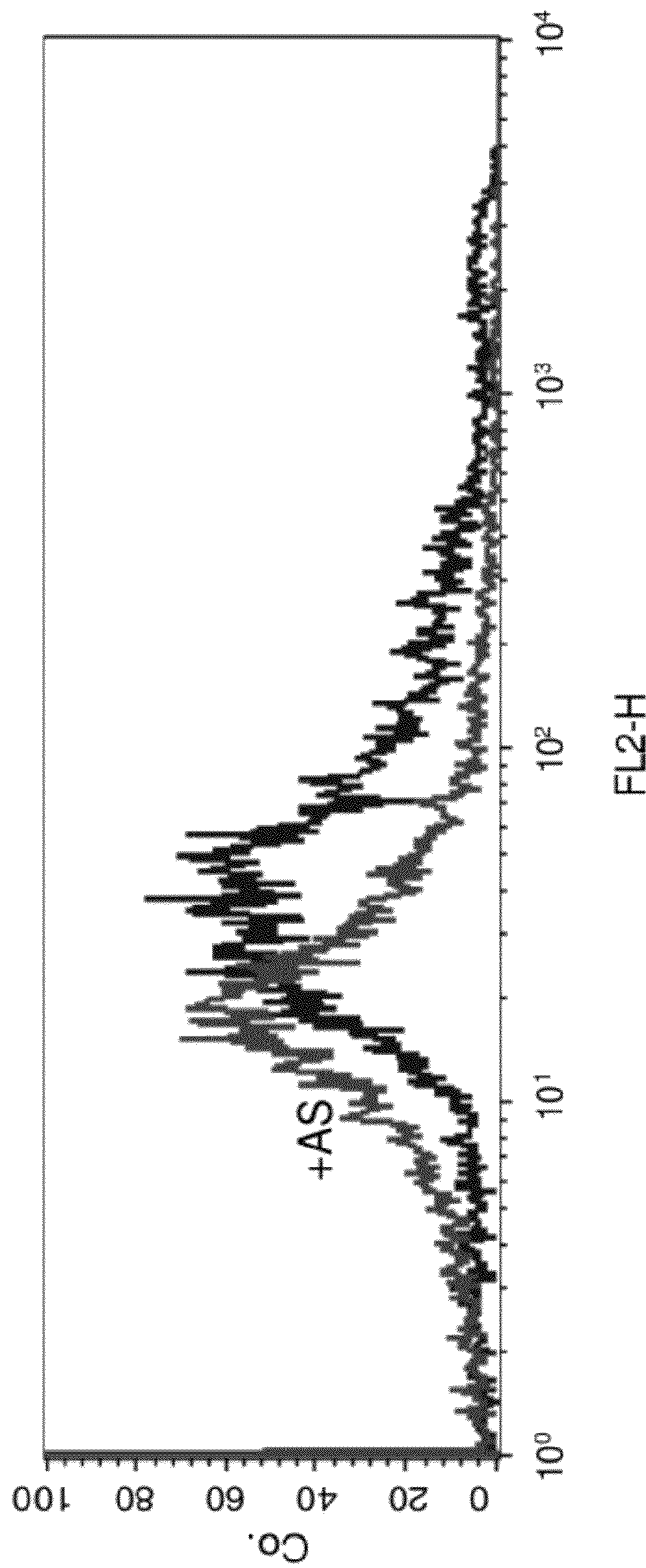

FIG. 16: $cPLA_2$ Antisense PPS Oligonucleotide Cocktail Treatment Decreased Unstimulated Superoxide Production by Resting Peritoneal Cells in Inflammation Site 24 Hours after Peritonitis Induction.

Shown is an example of detection of superoxide production by resting peritoneal cells isolated from sterile peritonitis mice assessed with 1 μM Dihydrorhodamine-123 without and with antisense treatment. Co.=counts.

FIG. 17A-17B: Effect of cPLA$_2$ Antisense PPS Oligonucleotide Cocktail Treatment on the Peritoneal Cell Composition in Mice with Sterile Peritonitis.

FIG. 17A: Peritoneal cell composition during sterile peritonitis.

FIG. 17B: Peritoneal cell composition post antisense treatment.

Abbreviations: ce. no., cell number; T., time; h, hours; neu, neutrophils; mac, macrophages; lymp, lymphocytes.

Abbreviations: Neu, neutrophils; mac, macrophages; lymp, lymphocytes; (means from 5 mice in each group).

Figure 18A:
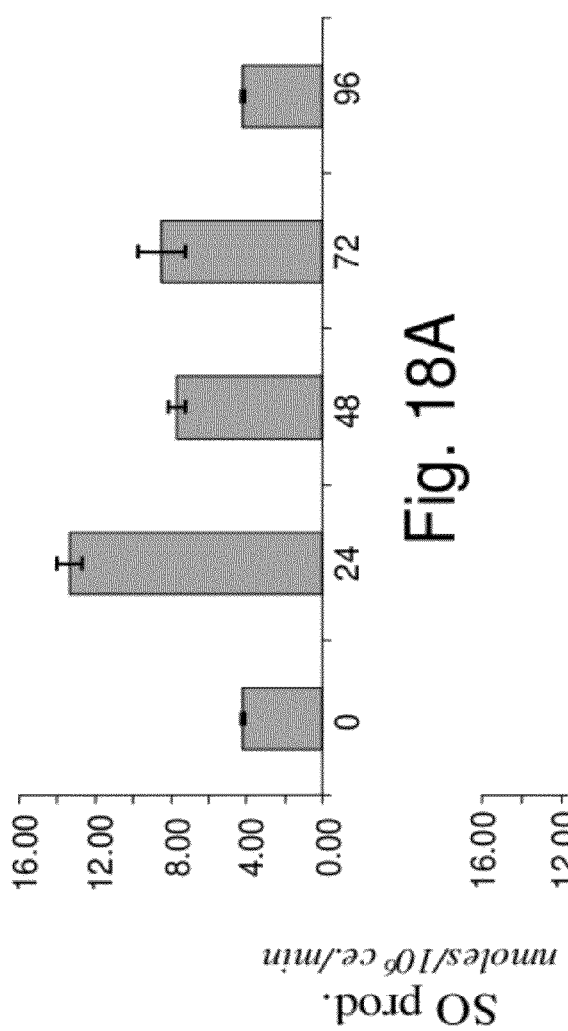
Figure 18B:
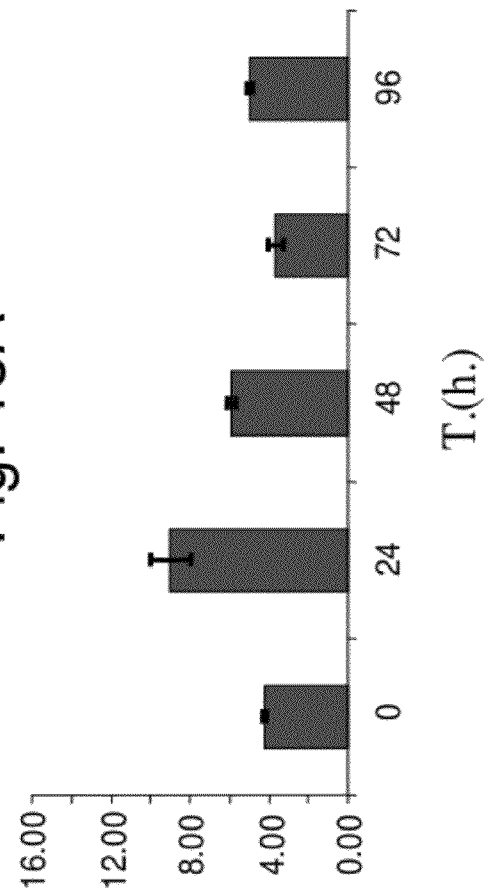

FIGS. 18A-18B: Effect of cPLA$_2$ Antisense PPS Oligonucleotide Treatment on Stimulated Superoxide Production (SO Prod.) by Peritoneal Cells During Sterile Peritonitis.

FIG. 18A: Stimulated superoxide production by peritoneal cells in mice with sterile peritonitis.

FIG. 18B: Stimulated superoxide production by peritoneal cells in mice with sterile peritonitis and treated with antisense oligonucleotides. Mean±SEM from 5 mice in each group. T.=time; h=hours.

FIGS. 19A-19B: cPLA$_2$ Antisense PPS Oligonucleotide Cocktail Treatment Decreased Peritoneal LTB$_4$ Levels.

FIG. 19A: LTB$_4$ levels in the peritoneum of sterile peritonitis mice.

FIG. 19B: LTB$_4$ levels in the peritoneum of sterile peritonitis mice treated with the cocktail.

Mean±SEM from 5 mice in each group. T.=time; h=hours.

FIGS. 20A-20B: cPLA$_2$ Antisense PPS Oligonucleotide Cocktail Treatment Decreased Peritoneal Neutrophils Count.

FIG. 20A: Number of neutrophils (Neu No) in the peritoneum of sterile peritonitis mice.

FIG. 20B: Number of neutrophils (Neu No) in the peritoneum of sterile peritonitis mice treated with the cocktail.

Mean±SEM from 5 mice in each group. T.=time; h=hours.

FIGS. 21A-21B: Accumulation of Antisense Oligonucleotides in Peritoneal Blood Cells 24 Hours after Injection.

FIG. 21A: Peritoneal blood cells, untreated.

FIG. 21B: Peritoneal blood cells treated with the antisense (as) oligonucleotides.

Upper panel: light microscope. Lower panel: confocal microscopy.

DETAILED DESCRIPTION OF THE INVENTION

In the present study, the inventors engineered six different antisense oligonucleotides against cytosolic phospholipase A$_2$ (cPLA$_2$) mRNA. As shown in the following Examples, each antisense by itself is significantly potent in inhibiting the expression of cPLA$_2$, while different combinations of the oligonucleotides totally inhibited cPLA$_2$ expression in the different phagocytic, as well as microglia cells from humans, mice and rats. Moreover, there is a striking correlation between the inhibition of cPLA$_2$ expression by the antisense oligonucleotides and the inhibition of superoxide production by NADPH oxidase, which has not been previously demonstrated.

Thus, the present invention provides antisense oligonucleotides directed against the open reading frame (ORF) of the cPLA$_2$ mRNA sequence (indicated in FIG. 1), and functional analogs, derivatives or fragments thereof, wherein the complementarity of said antisense oligonucleotide is within the region between nucleotides 145 to 400 of said ORF, and wherein said antisense oligonucleotide is capable of inhibiting the expression of the cPLA$_2$ protein.

As shown in the following Examples, the antisense oligonucleotides provided by the invention can also inhibit superoxide production by inhibiting NADPH oxidase activity.

As referred to herein, SEQ. ID. No. 7 relates to the cDNA sequence corresponding to the cPLA$_2$ mRNA sequence [GenBank No. M68874].

Said region between nucleotides 145 to 400 of the cPLA$_2$ mRNA is particularly useful for targeting, since it is much more efficient to prevent than to halt protein synthesis, once the process has already begun (the latter being the strategy used in U.S. Pat. No. 6,008,344, for most of its cPLA$_2$ antisense sequences). Therefore, the antisense oligonucleotides were designed as to target the region of translation site (beginning of the ORF).

Nonetheless, it is important to mention that antisense targeting is still very empirical, and a lot of experimentation is needed to find the specific sequence and the optimum conditions for most effective targeting. As described herein for example, the present inventors originally designed fourteen antisense oligonucleotides targeting the region between nucleotides 1.45-400 of the cPLA$_2$ sequence, corresponding to the beginning of the ORF, but only six of those worked efficiently, and were then studied in more detail.

Said antisense oligonucleotide directed against the 5' region of the open reading frame of the cPLA$_2$ mRNA sequence has the sequence as denoted by any one of SEQ. ID. No. 1, SEQ. ID. No. 2, SEQ. ID. No. 3, SEQ. ID. No. 4, SEQ. ID. No. 5, and SEQ. ID. No. 6, which sequences are detailed in Table 1.

As mentioned, the antisense oligonucleotides of the invention can be chemically modified, so as to possess improved endonuclease resistance. Any chemical modification which confers resistance towards endonucleases, such as, but not limited to phosphorothioation or 2-O-methylation, may be adopted.

Thus, a phosphorothioate modification may be present on the first three and/or the last three nucleotides of the oligonucleotides of the invention. In addition, another phosphorothioate modification may be found on the tenth nucleotide of said oligonucleotide, an inner pyrimidine, as for example in the oligonucleotides denoted by SEQ. ID. Nos. 4 and 5. Phosphorothioation of inner pyrimidines has been shown to increase stability and protect from endonuclease cleavage [Pirollo, K. F. et al. (2003) *Pharmacology & Therapeutics* 99:55-77]. The antisense oligonucleotides of the invention are partially phosphorothioated, and are thus less toxic than antisense oligonucleotides that have phosphorothioate modifications in all nucleotides.

Nevertheless, further modifications, like 2-O-methylation, may be found in the first three and/or the last three nucleotides of said oligonucleotide [EP 260,032]

As shown in Examples 5 to 7, the antisense oligonucleotides of the invention may be used as inhibitors of inflammation processes related to cPLA$_2$ expression and activity.

The antisense oligonucleotide of the invention is thus suitable for use in the treatment and/or prevention of any one of rheumatoid arthritis, ARDS, asthma, rhinitis, idiopathic pulmonary fibrosis, peritonitis, cardiovascular inflammation, myocardial ischemia, reperfusion injury, atherosclerosis, sepsis, trauma, diabetes type II, retinopathy, psoriasis, gastrointestinal inflammation, cirrhosis and inflammatory bowel disease, neurodegenerative diseases such as AD, PD and ALS, as well as brain ischemic and traumatic injury, i.e. in all diseases where oxidative stress has a significant role in its pathogenesis, and in which there is accelerated release of eicosanoids and superoxides by reactive microglia.

Although a study in human monocytes demonstrated that inhibition of cPLA$_2$ expression also inhibits NADPH oxidase activity [Li, Q. and Cathcart, M. K. (1997) id ibid.], another report had shown that resident peritoneal macrophages from cPLA$_2$-deficient mice can, under normal stimulation, release superoxide [Gijon, M. A. et al. (2000) *J. Biol. Chem.* 275: 20146]. In contrast, the present inventors have now demonstrated that the antisense oligonucleotides, which were efficient in inhibiting cPLA$_2$ expression in mice macrophages, were also efficient in inhibiting superoxide production in macrophages, as well as in monocytes, neutrophils and microglia cells. This disparity may be explained by the fact that often "knockout" animal models have normal phenotypes due to, for example, over expression and compensation of isoenzymes, and thus do not accurately mirror the effects of the lack of the gene (i.e., the protein or enzyme) in study. Most importantly, the present results were obtained using low levels of oligonucleotides of 1 μM (final concentration). It is important that the present antisense oligonucleotides are effective at low, non-toxic concentrations, which makes them suitable for use in clinical purposes, i.e., as a therapeutic agent for the treatment of conditions where inhibition of cPLA$_2$ is desirable, as discussed herein.

In addition, the antisense oligonucleotides of the invention are suitable for use in the treatment and/or prevention of conditions in which microglia cells are activated, for example by LPS, and release reactive oxygen species (ROS) and/or pro-inflammatory mediators, for example. Said conditions are selected from the group consisting of inflammations, infections, and ischemic disease.

The antisense oligonucleotide of the invention may also be used for inhibiting superoxide production and release. Usually, said inhibition is effectuated in neutrophils, monocytes and macrophages, preferably in neutrophils.

Activated neutrophils are the first cells arriving at the inflammation site, which then release high levels of eicosanoid and superoxides which accelerates the inflammatory process. Consequently, neutrophils are direct effectors of the pathogenesis of the various inflammatory diseases, and directly inhibiting their function is an efficient way to reduce inflammatory processes. Monocytes (and macrophages) are the second cell population to arrive at the site of inflammation, and thus their inhibition is also important to stall inflammation.

In addition, the antisense oligonucleotides of the invention may be used for inhibiting eicosanoid and ROS production released by microglia that are induced by amyloid β (Aβ) plaque formation or by other agents such as LYS or cytokines. ROS formation has been shown to be responsible for the dysfunction or death of neuronal cells that contributes to the pathogenesis of various neurological diseases.

By "analogs and derivatives" is meant the "fragments", "variants", "analogs" or "derivatives" of said nucleic acid molecule. A "fragment" of a molecule, such as any of the oligonucleotide sequences of the present invention, is meant to refer to any nucleotide subset of the molecule. A "variant" of such molecule is meant to refer a naturally occurring molecule substantially similar to either the entire molecule or a fragment thereof. An "analog" of a molecule can be without limitation a paralogous or orthologous molecule, e.g. a homologous molecule from the same species or from different species, respectively, i.e., an antisense oligonucleotide complementary to the equivalent region of the gene in a different species, which therefore may have slight changes in the sequence.

Further derivatives of the antisense oligonucleotides of the invention are those labeled, or conjugated to a reporter molecule, such that the antisense oligonucleotide of the invention may be traced and/or detected in the organism. Any label or reporter molecule that allow its detection may be suitable, like e.g. biotin, fluorescein, rhodamine, 4-(4'-Dimethylaminophenylazo)benzoic acid ("Dabcyl"); 4-(4'-Dimethylaminophenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives, radioactive labels, as well as metal particles (e.g. gold).

In a second aspect, the present invention relates to a pharmaceutical composition comprising as active agent at least one antisense oligonucleotide as defined in the invention, or functional analogs, derivatives or fragments thereof.

Thus, the antisense oligonucleotide of the invention is generally provided in the form of pharmaceutical compositions. Said compositions are for use by injection, topical administration, or oral uptake.

Alternatively, the pharmaceutical composition of the invention may comprise as active agent a combination of at least two antisense oligonucleotides as defined in the invention, or functional analogs, derivatives or fragments thereof. Preferably, said combination comprises the following oligonucleotides: SEQ. ID. No. 1 together with SEQ. ID. No. 3, or SEQ. ID. No. 1 together with SEQ. ID. No. 2, or SEQ. ID. No. 1 together with SEQ. ID. No. 6 or SEQ. ID. No. 1 together with SEQ. ID. No. 2 and SEQ. ID. No. 3, or SEQ. ID. No. 4 together with SEQ. ID. No. 6, or SEQ. ID. No. 2 together with SEQ. ID. No. 6, or SEQ. ID. No. 2 together with SEQ. ID. No. 3, or SEQ. ID. No. 3 together with SEQ. ID. No. 6.

In the Examples described herein below, it is clear how both inhibition of cPLA$_2$ and inhibition of superoxide production were much more efficient when the antisense oligonucleotides were used in combination of two or three together in the same reaction.

In one embodiment, the pharmaceutical composition of the invention is intended for the treatment of inflammation processes related to cPLA$_2$ expression and/or free radical release by phagocyte NADPH oxidase.

In another embodiment, the pharmaceutical composition of the invention is intended for the treatment of inflammatory conditions, wherein said inflammatory conditions may be any one of rheumatoid arthritis, ARDS, asthma, rhinitis, idiopathic pulmonary fibrosis, peritonitis, cardiovascular inflammation, myocardial ischemia, reperfusion injury, atherosclerosis, sepsis, trauma, diabetes type II, retinopathy, psoriasis, gastrointestinal inflammation, cirrhosis and inflammatory bowel disease, neurodegenerative diseases such as AD, PD and ALS, as well as brain ischemic and traumatic injury, i.e. in all diseases where oxidative stress has a significant role in its pathogenesis, and in which there is accelerated release of eicosanoids and superoxides by reactive microglia.

In a further embodiment, the pharmaceutical composition of the invention is intended for the treatment of conditions related to Aβ plaque accumulation. Said conditions are generally neurodegenerative diseases, preferably Alzheimer's, Parkinson's, ALS, or brain ischemic and, traumatic injury.

The pharmaceutical composition of the invention is also intended to be used in the treatment and/or prevention of conditions, for example exposure to LYS, in which microglia cells are activated and release ROS and/or pro-inflammatory mediators (eicosanoid). Said conditions are selected from the group consisting of inflammations, infections, and ischemic disease.

Preferred uses of the pharmaceutical compositions of the invention by injection are subcutaneous injection, intraperitoneal injection, intravenous and intramuscular injection.

The pharmaceutical composition of the invention generally further comprises diluent, and/or a buffering agent, i.e. an agent which adjusts the osmolarity thereof, and optionally, one or more carriers, stabilizers, excipients and/or additives as known in the art, e.g., for the purposes of adding flavors, colors, lubrication, or the like to the pharmaceutical composition.

A preferred buffering agent is Tris, consisting of 10 mM Tris, pH 7.5-8.0, which solution is also adjusted for osmolarity.

For in vivo use the antisense oligonucleotides are suspended distilled water or in sterile saline.

Carriers may include starch and derivatives thereof, cellulose and derivatives thereof, e.g., microcrystalline cellulose, xantham gum, and the like. Lubricants may include hydrogenated castor oil and the like.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein.

Pharmaceutical compositions for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile, aqueous solutions which may also contain buffers, diluents and other suitable additives such as, but not limited to, penetration enhancers, carrier compounds and other pharmaceutically acceptable carriers or excipients.

The pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In, general the formulations are prepared by uniformly and intimately bringing into association the active ingredients with liquid carriers or finely divided solid carriers or both, and then, if necessary, shaping the product. Such compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The pharmaceutical composition of the invention may further comprise other active agents, e.g. antibiotics, analgesics and the like.

In another aspect, the present invention provides the use of the antisense oligonucleotide as defined in the invention, for the preparation of a pharmaceutical composition for the treatment and/or prevention of inflammatory conditions, wherein said inflammatory conditions may be any one of rheumatoid arthritis, ARDS, asthma, rhinitis, idiopathic pulmonary fibrosis, peritonitis, cardiovascular inflammation, myocardial ischemic, reperfusion injury, atherosclerosis, sepsis, trauma, diabetes type retinopathy, psoriasis, gastrointestinal inflammation, cirrhosis and inflammatory bowel disease neurodegenerative diseases such as AD, PD, and ALS, as well as brain ischemic and traumatic injury, i.e. in all diseases where oxidative stress has a significant role in its pathogenesis, and in which there is accelerated release of eicosanoids and superoxides by reactive microglia.

Furthermore, the present invention provides the use of an antisense oligonucleotide as defined in the invention for the treatment of conditions associated with $cPLA_2$ activation, as well as for the treatment and/or prevention of conditions related to Aβ plaque accumulation. Generally said conditions are neurodegenerative diseases, selected from the group consisting of Alzheimer's disease, Parkinson's disease, ALS, and brain ischemic and traumatic injury.

Hence, the present invention presents a method of treatment of conditions associated with $cPLA_2$ activation, comprising administering a therapeutically effective amount of at least one antisense oligonucleotide as defined in the invention, or compositions comprising thereof, to a subject in need.

Said therapeutic effective amount, or dosing, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$, found to be effective in in vitro as well as in in vivo animal models. In general, dosage is from 0.01 μg to 10 mg per kg of body weight, and may be given once or more daily, weekly, monthly or yearly, or even once every 2 to 20 years. Persons of ordinary skill in the art can easily estimate repetition rates for dosing based on measured residence times and concentrations of the antisense oligonucleotide in bodily fluids or tissues.

Following successful treatment, it may be desirable to have the patient undergo maintenance therapy to prevent the recurrence of the disease state, wherein the oligonucleotide is administered in maintenance doses, ranging from 0.01 μg to 10 mg per kg of body weight, once or more daily.

As demonstrated in the following Examples 5 to 7, optimal dosage used for treatment of the inflammatory conditions is 1-2 mg/kg/day given daily for between 5 up to 14 days (Example 5), or given in one or two doses of 1-2 mg/kg/day after inflammation (Examples 6 and 7).

The use of antisense oligonucleotides for inhibiting $cPLA_2$ expression is an innovative treatment for local inflammatory diseases, since it will inhibit specifically the elevated $cPLA_2$ at the site of inflammation and will not affect normal $cPLA_2$ expression. This treatment is potentially even more effective when affecting also the activity of activated or primed phagocytes involved in the pathogenesis of such diseases, since these cells secrete high levels of eicosanoids and superoxides, which accelerate the inflammation process.

Therefore, the present invention also provides a method of treatment of inflammatory conditions, wherein said inflammatory conditions are any one of rheumatoid arthritis, ARDS, asthma, rhinitis, idiopathic pulmonary fibrosis, peritonitis, cardiovascular inflammation, myocardial ischemia, reperfusion injury, atherosclerosis, sepsis, trauma, diabetes type II, retinopathy, psoriasis, gastrointestinal inflammation, cirrhosis and inflammatory bowel disease, neurodegenerative diseases such as AD, PD and ALS, as well as brain ischemic and traumatic injury, i.e. in all diseases where oxidative stress has a significant role in its pathogenesis, and in which there is accelerated release of eicosanoids and superoxides by reactive microglia, comprising administering a therapeutically effective amount of at least one antisense oligonucleotide as defined in the invention, or compositions comprising thereof, to a subject in need.

In addition, involvement of $cPLA_2$ in the regulation of superoxide production by NADPH oxidase in microglia cells suggests that $cPLA_2$ antisense oligonucleotides may be used in the treatment of neurodegenerative diseases, selected from the group consisting of Alzheimer's disease, Parkinson's disease, ALS, and brain ischemic and traumatic injury.

Likewise, the present invention also provides a method for the treatment and/or prevention of conditions in which microglia cells are activated, exposed to LPS for example, and release ROS and/or pro-inflammatory mediators, and wherein aid conditions are selected from the group consisting of inflammations, infections, and ischemic disease. Said method comprises administering a therapeutically effective amount of at least one antisense oligonucleotide as defined in the invention, or compositions comprising thereof, to a subject in need.

As a final aspect, the present invention provides a method of treatment of neurodegenerative diseases, as well as brain damage (caused by stroke or trauma, for example), comprising administering a therapeutically effective amount of at least one antisense oligonucleotide as defined in the invention, or compositions comprising thereof, to a subject in need. Said conditions are generally neurodegenerative diseases, preferably Alzheimer's and Parkinson's disease, or brain ischemic and traumatic injury, in which there is accelerated release of eicosanoid and superoxides by reactive microglia.

Various methods of administration may be used for delivering the antisense oligonucleotide of the invention to a subject in need. Oligonucleotides may be delivered via, intravenous (i.v.), intramuscular (i.m.) intraperitoneal (i.p.) injections, orally (in liquid form or prepared as dosage unit forms like capsules, pills, lozenges, etc.). In order to be effective therapeutically, oligonucleotides should be prepared in a way that would enable their stability in the system following injection, or vet more preferably, following oral administration.

Alternatively, the oligonucleotides of the invention may also be delivered via transdermal delivery using patches, ointment or cream.

In addition, pharmaceutical compositions comprising as active agent the antisense oligonucleotides described, in the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful far oral administration.

As shown in the following Examples, preliminary trials with three different models of inflammation in mice and rats (arthritis, ARDS and peritonitis), demonstrate the effectiveness of the specific $cPLA_2$ antisense oligonucleotides as anti-inflammatory treatment.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

EXAMPLES

Experimental Procedures

General Methods of Molecular Biology

A number of methods of the molecular biology art are not detailed herein, as they are well known to the person of skill in the art. Such methods include PCR, expression of cDNAs, transfection of mammalian cells, and the like. Textbooks describing such methods are, e.g., Sambrook et al. (1989) *Molecular Cloning, A Laboratory Manual*, Cold Spring Harbor Laboratory, ISBN: 0879693096; F. M. Ausubel (1988) *Current Protocols in Molecular Biology*, ISBN: 047150338X, John Wiley & Sons, Inc. Furthermore, a number of immunological, techniques are not in each instance described herein in detail, like for example Western Blot, as they are well known to the person of skill in the art. See, e.g., Harlow and Lane (1988) *Antibodies: a laboratory manual*. Cold Spring Harbor Laboratory.

Oligonucleotides

TABLE 1

Oligonucleotides used in the following examples

| Oligon. | Sequence 5'-3' | Reference | Sequence ID. No. |
|---------|----------------|-----------|------------------|
| C2 | ttcaaaggtctcattccaca | — | SEQ. ID. No. 1 |
| C3 | cactataatgtgctggtaag | — | SEQ. ID. No. 2 |
| C4 | caaaacattttcctgattagg | — | SEQ. ID. No. 3 |
| C8 | cacagggtttatgtcattat | — | SEQ. ID. No. 4 |

TABLE 1-continued

Oligonucleotides used in the following examples

| Oligon. | Sequence 5'-3' | Reference | Sequence ID. No. |
|---|---|---|---|
| C9 | ccgtaaacttgtgggaatac | — | SEQ. ID. No. 5 |
| C10 | gctgtcaggggttgtag | — | SEQ. ID. No. 6 |
| P1 | gtaaggatctataaatgacat | [Roshak et al. (1994) id ibid; Muthalif et al. (1996) id ibid; Marshall et al (1997) id ibid; Anderson et al. (1997) id ibid.] | SEQ. ID. No. 8 |
| P2 | cccctttgtcactttggtg | [Li and Cathcart (1997) id ibid] | SEQ. ID. No. 9 |
| IS1 | gcccaaaactctgttgaa | [U.S. Pat. No. 6,008,344] | SEQ. ID. No. 10 |
| IS2 | ttgtgaaccagaaacgcc | [U.S. Pat. No. 6,008,344] | SEQ. ID. No. 11 |

Note:
the underline shows phosphorothioated nucleotides.

Example 1

Synthesis of Anti-cPLA$_2$ Antisense Oligonucleotides

Fourteen different partially phosphorothioated [Stein et al. (1988) *Nucleic Acids Res.* 16:3209-3221] oligonucleotides against cPLA$_2$ were originally synthesized. Prior to use, the oligonucleotides were purified by HPLC and tested for purity by mass spectrometry (Sigma, UK). Prior to selection, the sequences were analyzed by screening for uniqueness using the Blast program and were also tested for lack of secondary structure and oligo pairing using Mulfold [Jaeger, J. A. (1989) *Methods Enzymol.* 183: 281-306].

Preliminary experiments (not shown) demonstrated that from those fourteen, only six oligonucleotides were found to be efficient in inhibiting cPLA$_2$ expression, and their sequences are detailed in Table 1 above.

The fact that only six antisense oligonucleotides displayed significant activity suggested that these have increased specificity for the target sequence. The remaining eight oligonucleotides were used in the experiments as controls.

The oligonucleotides carried phosphorothioate modifications on the last 3 bases at both 5' and 3' ends (as indicated by underline, Table 1), and were engineered using computer based approach using RNADraw V1.1 [Mazura Multimedia. Sweden] for the first 400 hundred base pairs (N-terminal) of cPLA$_2$ mRNA (Table 1).

The partially phosphorothioated oligonucleotides (PPS) are less toxic and more specific than the phosphorothioated oligonucleotides, but similar in their stability and cellular uptake. Some PPS contain GGGG (C10) and GGG (C8 and C9) which have been shown to increase cellular uptake (see Table 1). PPS C8, C9 also contain phosphorothioated on inner pyrimidines (t) which have been shown to increase stability and protect from endonuclease cleavage (Table 1, underlined). Five of the antisense oligonucleotides did not contain CpG, which have been shown to stimulate immune responses. In all of the experiments presented herein, naked PPS were added since in this form they can be used for in vivo treatment [Pirollo. K. F. et al. (2003) id ibid.], in contrast to the published studies in vitro, which used different delivery systems to increase the antisense uptake. Hence, all the clinical trials with antisense oligonucleotides are carried out with naked oligonucleotides. For example, an in vivo clinical trial did not require cationic lipids for oligonucleotide delivery against Bcl-2 in cancer patients, in contrast to the experiments performed in tissue culture [Jansen, B. et al. (2000) *Lancet* 356: 1728-1733]. This is usually the case in in vivo assays, and to date it is not well understood why a vector does not appear to be necessary. One hypothesis is that the oligonucleotides interact with circulating proteins, which both protect them against degradation, and serve as carriers in ways not yet understood [Dias, N. and Stein, C. A. (2002) *Eur. J. Pharmac and Biopharmac.* 54: 263-269].

As shown in FIGS. 3-7, there is a clear correlation between inhibition of cPLA$_2$ expression by the PPS antisense oligonucleotides and stimulated production of superoxides. Each PPS oligonucleotide caused significant inhibition of cPLA$_2$ protein expression in different phagocytic cell types, and their combinations caused significantly improved inhibition.

As shown in FIGS. 3 and 4, the PPS antisense oligonucleotides of the invention are far more efficient than those previously reported [U.S. Pat. No. 6,008,334; Roshak et al. (1994) id ibid; Muthalif et al. (1996) id ibid; Marshall et al (1997) id ibid; Anderson et al, (1997) id ibid; Li, Q. and Cathcart, M. K. (1997) id ibid.; Zhao. X. et al. (2002) id ibid.]. Moreover, in the previous reports, these antisense oligonucleotides were tested only for their capacity to inhibit mRNA synthesis [U.S. Pat. No. 6,008,334]

The effect of the number (and kind) of modifications at the two ends of the oligonucleotides was also evaluated (data not shown). The rank order of the efficiency in inhibiting cPLA$_2$ expression and NADPH oxidase observed was as follows: PPS with 3 modifications>PPS with 2 modifications>PPS with 1 modification>no modification.

The PPS antisense oligonucleotides were more efficient in inhibiting cPLA$_2$ protein expression in the phagocytic cells, as shown for monocytes, than endothelial or epithelial cells (data not shown). This phenomenon has advantages especially regarding treatment of inflammation directly affecting the phagocyte at the site of inflammation, without affecting the organ.

Example 2

Effect of cPLA$_2$ Antisense Oligonucleotides on cPLA$_2$ Expression and Superoxide Production in Peripheral Blood Human Monocytes The expression of cPLA$_2$ protein was analyzed by Western blot analysis using antibodies against cPLA$_2$ that were raised by the inventors and which are much more efficient than those available on the commercial market (FIG. 2).

The effect of the different PPS antisense oligonucleotides and their combinations on cPLA$_2$ expression and on superoxide production was studied in peripheral blood human monocytes (FIGS. 3 and 4) and in murine macrophages (FIG. 5). Naked (free of transfection solutions like lipofectin, etc.) PPS antisense oligonucleotides (final concentration of 1 μM) were added to the cell suspension in RPMI containing 10% FCS for 16 h at 37° C. The same cells were analyzed for superoxide production stimulated with 5 ng/ml PMA (by cytochrome c reduction) and for the expression of $cPLA_2$ in cell lysates (by Western blot analysis). As shown, each of the PPS antisenses caused between 50-75% inhibition of superoxide production, which is in correlation with their effect on inhibiting $cPLA_2$ expression. The level of $cPLA_2$ was quantitated by densitometry in a reflectance mode (Hoefer, Hoefer Scientific Instruments, San Francisco, USA). The correlation between these two parameters is demonstrated in FIG. 6.

As shown in FIGS. 3 and 4, respectively, P1 [Roshak et al. (1994) id ibid; Muthalif et al. (1996) id ibid; Marshall et al (1997) id ibid; Anderson et al. (1997) id ibid.] and P2 [Li, Q. and Cathcart. M. K. (1997) id ibid.], and IS1 and 152 [U.S. Pat. No. 6,008,334] did not have any effect either on $cPLA_2$ expression or on superoxide production. Most importantly, oligonucleotides IS1 and IS2, were reported, in U.S. Pat. No. 6,008,334, to cause 100% and 92% inhibition of mRNA expression, respectively. However, their effect was analyzed only by inhibition of mRNA expression and not by inhibition of $cPLA_2$ protein expression.

In their original publications, P1, P2, IS1 and IS2 were synthesized with phosphorothioate modifications in all bases. The present inventor found that, when fully phosphorothioated, these oligonucleotides were toxic to the cells, and caused the killing of about 60-70% of the cells after 16 hours of incubation (data not shown). These results are consistent with a previous report showing that oligonucleotides with phosphorothioate modifications in all bases are much more toxic [Pirollo, K. F. et al. (2003) id ibid.]. Thus, it is important to note that, for this study, P1, P2, IS1 and IS2, differently from the original oligonucleotides, were synthesized with phosphorothioate modifications only in the first and last three bases, in order to more accurately compare their effect to the effect of the PPS antisense oligonucleotides synthesized by the present inventor.

The results shown in FIGS. 2 and 3 demonstrate that the antisense oligonucleotides synthesized (and claimed) by the inventor are superior to the oligonucleotides described in the literature. In particular, it may be highlighted that the former are:
a. Less toxic;
b. Much more potent in inhibiting $cPLA_2$ protein expression.

The antisense oligonucleotides are especially preferred, compared to P1, P2, IS1 and IS2 since they may be introduced into the cells and perform their activity without cell delivery systems like lipofectin.

Example 3

Effect of $cPLA_2$ Antisense Oligonucleotides on $cPLA_2$ Expression and Superoxide Production in Peripheral Blood Human Neutrophils The effect of the different PPS antisense oligonucleotides, and their combinations, on $cPLA_2$ expression and on superoxide production was studied in peripheral blood human neutrophils. Naked antisense oligonucleotides were added (at 1 µM final concentration) to $2\times10^5$ neutrophils for 6 h at 37° C. Neutrophils (95% purity) were isolated by Ficoll/Hypaque centrifugation, dextran sedimentation and hypotonic lysis of erythrocytes [Levy, R. et al. (2000) *Blood* 9:660-665]. As shown in FIG. 7, there was a slight though significant ($P<0.05$) inhibition of superoxide production even after 6 hours of incubation with the neutrophils, in another experiment, a similar effect was shown after 16 h of incubation (data not shown).

Inhibition of superoxide production by the various oligonucleotide antisenses was significantly improved when the cells were stimulated by physiological agonists such as fMLP, opsonized zymosan (OZ) (FIG. 8), LTB4, angiotensin II or AGEs (advanced glycation end products) (data not shown) which bind specific receptors on cell membranes.

The effect of the PPS was significantly higher when neutrophils were purified from patients with inflammatory diseases (like rheumatic arthritis, asthma or sepsis, data not shown), than when the neutrophils were from healthy controls. This phenomena is consistent with the inventor's earlier study [Levy, R. et al. (2000) id ibid.] which reported that the level of $cPLA_2$ in neutrophils is higher during the diseases indicating increase rate of synthesis, and thus more prone to targeting.

It is important to note that the experiments portrayed in FIGS. 3 to 6 were performed with the non-physiological stimulant PMA, an extremely potent activator of NADPH oxidase that bypasses the receptors and acts on PKC. This enabled the analysis of the role of the antisenses directly on NADPH oxidase, since under these conditions the effect of the expression of the different receptors and their binding to stimulants is eliminated.

Example 4

Effect of $cPLA_2$ Antisense Oligonucleotides on $cPLA_2$ Expression and Superoxide Production in Rat Microglia The effect of the antisenses and their combinations was studied on microglia isolated from rat brain. The PPS antisense oligonucleotides were added (at 1 µM final concentration) to microglia cells for 16 h (similar to the conditions used for monocytes). There was a significant inhibition of $cPLA_2$ protein expression. The cells were stimulated with 2 mg/ml PMA or with 10 µM of Amyloid β, and superoxide production was analyzed by the fluorescence probe Amplex Red. As shown in FIG. 9, the antisenses caused significant inhibition of superoxide production, in correlation with $cPLA_2$ protein expression. Interestingly, antisense C8, which did not, match the rat sequence by 1 base, did not cause inhibition of superoxide production, indicating the high specificity of the antisenses. Inhibition was much higher when the cells were stimulated with Amyloid β. Incubation of microglia for 48 h with the antisense oligonucleotides caused higher inhibition of $cPLA_2$ expression and of superoxide production (data not shown). The results are of particular importance since Amyloid β plays an important role in the pathogenesis of brain and neurodegenerative diseases, such as Alzheimer.

Incubation of all cell types with ×150 antisense concentration was not toxic to the cells and did not affect cell functions which are not regulated by $cPLA_2$ (data not shown).

Example 5

Animal Model of Inflammation: Collagen-Induced Arthritis

Collagen-induced arthritic (CIA) is an experimental in odd of autoimmune arthritis that has many clinical and pathological similarities to rheumatoid arthritis (RA), CIA is induced, by immunizing susceptible animals (e.g. DBA black mice) with type II collagen (CII) as described [Bendele, A. M. et al. (2000) *Arthritis & Rheumatism*, 43:2648-58]. All mice were maintained in a specific pathogen-free environment, and fed standard mouse chow and water. Chick CII (Sigma-Aldrich, 2 mg/ml) was dissolved overnight at 4° C. in 10 mM acetic acid and combined with an equal volume of CFA (complete Freund's adjuvant). CFA was prepared by mixing 100 mg of heat-killed *M. tuberculosis* (H37Ra, Difco, Detroit, Mich., USA) with 20 ml of incomplete Freund's adjuvant (Sigma-Aldrich, St. Louis, Mo., USA). Mice (aged 7 to 10 weeks)

were injected intradermally at the base of the tail and booted at day 7 or 21. Control mice were treated with CFA without CII. The severity of arthritis was monitored by direct examination with a digital caliper according to the following scale: grade 0, no swelling; 1, slight swelling and erythema; pronounced inflammation; and 3, joint rigidity. Each limb was graded, giving a maximum possible score of 12 per animal. Fluid from animal paws was aspirated to determine cytokines (mRNA and protein level) and white blood cells. After sacrifice, paws were collected, fixed, decalcified, and paraffin embedded. Sections were stained with hematoxylin and eosin and scored according to the following scale: 0, no inflammation; 1, slight thickening of the synovial cell layer and/or seine inflammatory cells in the sublining; 2, thickening of the synovial lining, infiltration of sublining, and localized cartilage erosions; and 3, infiltration in the synovial space, pannus formation, cartilage destruction, and bone erosion.

Detection of anti-CII antibodies: ELISA for antibodies to CII was performed by HRP-conjugated secondary antibody specific for IgG1, IgG2a, IgG2b, IgG3, or IgM and IgA.

Cell isolation: Positive selection of splenocyte subsets of synovial cells were performed using specific biotin-conjugated antibodies against CD11b, CD3, CD4, and CD8, and biotin binder Dynabeads. After positive selection of CD11b$^+$ and CD3$^+$ synovial cells, synovial cells were incubated with biotin CD45 and negatively selected using an excess of avidin-magnetic beads. The remaining CD45-negative cells were used for RNA extraction. Synovial fluid leukocytes were obtained from synovial effusions and purified by Ficoll-Hypaque density gradient centrifugation.

The model of CIA was successfully developed by the inventors, as demonstrated, e.g. by the swollen limb of an exacerbated CIA mouse compared to the limb of a control mouse (FIG. 10A). Histological assessment of the CIA mouse limb FIG. 10B) was in correlation with the severity of arthritis, monitored by direct examination of the limb as presented in FIG. 10A. Infiltration of inflammatory cells (especially neutrophils) is shown in a joint section of a CIA mouse (FIG. 10C). CIA mice showed severe difficulties in walking (data not shown).

Based on preliminary experiments performed with various PPS concentrations and combinations, the optimal concentration of 2 mg/Kg was defined, for a combination of 3 different PPS (2, 4 and 10), also referred to herein as cocktail. This concentration is within the range used for human therapy and in animal models.

For treatment of the inflammatory condition, sterile stock of antisenses (100 μM) is dissolved in sterile saline at the desired concentrations, and injected to sick mice either i.v., intradermally at the base of the tail, or at the inflamed joints.

As shown in FIG. 11, intravenous injection of 2 mg/kg of the "cocktail" every day for 14 days caused significant remission of the arthritis, as detected by a reduction in swelling of the limb (FIG. 11A), by disease severity score, by full recovery of the mice ability to move and to run freely (data not shown), and by reduction in serum IL-6 and TNFα levels (FIG. 11B).

Example 6

Animal Model of Inflammation: Peritonitis

Model mice peritonitis is being developed in CD1 mice by injection of Candia as previously described [Levy, R. et al. (1989) *J. Biol. Regul. Homeost. R Agents* 3:5-12], or by injection of different doses of gram positive bacteria peritonitis will be induced with lethal doses of candida or bacteria (*S. epidermitis*) or gram negative (*E. Coli*) which cause animal killing and with moderate doses which cause a moderate disease. The 50% lethal doses were determined as $6 \times 10^8$ CFU for *S. epidermitis* and $1.5 \times 10^7$ for *E. coli*. The markers for infection and/or inflammation are: the number and population of blood cells in the peritonitis area, the concentration of inflammatory cytokines in the blood, such as TNFα. IL1 and IL6, and histological analyses of peritoneal sections. Mice injected with a lethal dose of bacteria are treated with antisenses 2 h after injection of the bacteria followed by antisenses injection in different time intervals. In these experiments, the effect of antisenses on mice survival is evaluated. For mice injected with lower doses of bacteria, the effect of antisenses (injected as described) is evaluated, on the pathology by the infection and/or inflammation markers.

Example 7

Animal Model of Inflammation: Sterile Peritonitis

A model of sterile peritonitis was developed in ICR mice by intraperitoneal injection of 3 ml sterile 4% thioglycollate (TG) as described previously [Segal, B. H. et al. (2002) *J Leukoc Biol* 71:410]. Assessment of inflammation was determined by the number and population of blood cells in the peritonitis cavity, the concentration of LTB$_4$ and the presence of inflammatory cytokines, TNFα and IL6, in cell free peritoneal fluid and in serum. 10 ml of sterile PBS were injected to the peritoneal cavity in order to collect the cells. The number of cells was determined by microscopy after trypan blue staining. The composition of the cell population was determined by FACS using antibodies against anti mouse neutrophils (MCA771F), anti mouse macrophages (F4/80) and anti mouse lymphocytes (CD3). The composition of the cell population was also determined under microscopy after Giemsa staining. FIGS. 12A-12B present the changes in white blood cell count (FIG. 12A) and cell population (FIG. 12B) during 4 days of sterile peritonitis. High levels of neutrophils were detected 24 h after TG injection, which were later replaced by monocyte macrophages. There was it significant elevation in stimulated phagocyte superoxide production, with the highest rate at 24 h post peritonitis induction.

The levels of LTB4 in the serum and in the peritoneal cavity during 24 h of sterile peritonitis are demonstrated in FIGS. 13A-13B. 1 hour after the induction of peritonitis there was a significant elevation of LTB4 levels in the blood. LTB4 levels stayed high during 5 h and than decreased to half after 8 hours. At 16 h after peritonitis induction, LTB4 could not be detected in the blood. A similar pattern was observed in the peritoneal cavity, but the decay was slower and only after 24 h, LTB4 ceased, to be detected.

According to the present results and consistent with the literature, the first cells to accumulate in the peritonitis model were neutrophils. Thus, in the first set of experiments the effect of the antisense oligonucleotides was analyzed primarily on neutrophil accumulation and activity, after 24 h of induction of sterile peritonitis. Two doses of a specific combination of PPS antisense oligonucleotides against cPLA$_2$ (the "cocktail") dissolved in sterile water (0.2 ml) were administered i.v. in the tail of the mice 1 h and 4 h after induction of peritonitis. As demonstrated in FIGS. 14A-14O (results of two mice) this treatment caused a significant reduction in the number of neutrophils present in the peritoneal cavity (represented as cell number and cell population distribution detected by FACS analysis) and a slight inhibition of stimulated superoxide production by the peritoneal cells 24 h after induction of inflammation. The efficiency of the cocktail on reduction of peritoneal recruited neutrophils and on superoxide production in 34 mice compared to 34 untreated mice with sterile peritonitis is presented in FIGS. 15A-15B. Superoxide release from unstimulated cells is of great importance since it reflects the behavior of the peritoneal cells in the peritoneum cavity. Thus, the release of superoxide from resting cells was assessed with the fluorescent probe Dihydrorhodamine-123 (1 mM) which is a very sensitive method and can detect low levels of superoxide. As shown in the representative results in FIG. 16, the cocktail treatment for 24 h after induction of peritonitis significantly decreased the release of superoxides by peritoneal cells.

The effect of the antisense oligonucleotide treatment was studied on peritoneal cell population during 4 days of sterile peritonitis. The number of recruited neutrophils was dramatically reduced and that of macrophages was significantly lower in the peritoneum of treated mice during the 4 days of peritonitis (FIG. 17A-17B). Stimulated superoxide production by the peritoneal cells of the antisense-treated mice was significantly lower than in the untreated mice during the four days of peritonitis (FIGS. 18A-18B).

The antisense cocktail treatment reduced the levels of $LTB_4$ in the peritoneal cavity as measured during 24 h after induction of peritonitis (FIGS. 19A-19B) in correlation with the reduction of neutrophils recruited to peritoneal cavity (FIGS. 20A-20B).

Accumulation of antisense oligonucleotides in peritoneal blood cells 24 h after i.v. injection was detected using fluorescently labeled antisense oligonucleotides (labeled with FITC at the last nucleotide) (FIGS. 21A-21B). Distribution of the fluorescent antisense oligonucleotides in the different organs by histological section was also analyzed (data not shown). In further experiments, different antisense overdoses were administered, in order to determine their toxicity. A cocktail ×100 was not toxic to the mice (data not shown).

Example 8

Animal Model of Inflammation: Experimental Acute Lung Injury Induced by:
1—LPS/Zymosan Administration, Mice are anesthetized and mechanically ventilated. During the experiments, oxygen gas is supplied continuously to the ventilatory system. One minute prior to intravenous (i.v.) administration, two deep inhalations (3× tidal volume) are delivered to standardize volume history and measurements are made as baseline. Mice then receive 3 mg/kg of LPS from *Escherichia coli* O111:B4 (Sigma Chemical Co., St. Louis, Mo.) i.v. Two hours later, 10 mg/kg of zymosan A from *Saccharomyces cerevisiae* (Sigma) are administered i.v. In saline-treated group, animals receive saline instead of LPS and zymosan in the same manner, and serve as controls. In all groups, measurements are made at 30 minute intervals for 4 hours. In some animals, the observation period extended up to 6 hours. To assess the development of lung injury physiologically, EL (a reciprocal of lung compliance) is measured. Tracheal pressure (Ptr), flow and volume (V) will be measured. EL and lung resistance (RL, data not shown) are calculated by adjusting the equation of motion: Ptr=ELV+RL (dV/dt)+K, where K is a constant. Changes in EL reflect lung parenchymal alterations and stiffening of the lungs.

2—HCl Aspiration.

After baseline measurements, anesthetized and mechanically ventilated mice receive 2 ml/kg of HCl (pH=15) i.t., followed by a bolus of air (30 ml/kg). In saline-treated group, animals receive saline instead of HCl in the same manner and serve as controls. In all groups measurements are made at 30 minute intervals for 2 hours. In some animals, the observation period is up to 5 hours. EL measurement is a physiologic parameter to assess acute lung injury.

Assessment of pulmonary edema—At the end of experiment, the lung wet/dry mass ratios are calculated to assess pulmonary edema. After the trapped blood is drained from the excised lungs, measurements of the lung wet mass are made. The lungs are then heated at 90° C. to constant mass in a gravity convection oven for 72 h and the residue weighed as the lung dry mass.

Bronchoalveolar lavage fluid—At the end of experiment, bronchoalveolar lavage (BAL) is performed (using 5×1 ml phosphate-buffered saline) in each group. In each animal, 90% (4.5 ml) of the total injected volume is consistently recovered. After BAL fluid is centrifuged at 450 g for 10 minutes, the total and differential cell counts of the BAL fluid is determined from the cell fraction. The supernatant is stored at −70° C. until measurement of protein content. The concentration of protein is measured by Lowry's method using bovine serum albumin as a standard.

Thromboxane and leukotriene measurement—is determined by using enzyme immunoassay (EIA) kits.

The invention claimed is:

1. An antisense oligonucleotide directed against the 5' region of the open reading frame of the cytosolic phospholipase $A_2$ (cPLA$_2$) mRNA sequence, wherein the antisense oligonucleotide consists of a nucleotide sequence selected from the group consisting of SEQ ID NO:1, SEQ ID NO:2, SEQ ID NO:3, SEQ ID NO:4, SEQ ID NO:5, and SEQ ID NO:6.

2. The antisense oligonucleotide of claim 1, wherein the first three and/or the last three nucleotides of said oligonucleotide have a phosphorothioate modification.

3. The antisense oligonucleotide of claim 1, wherein the tenth nucleotide of said oligonucleotide have a phosphorothioate modification.

4. The antisense oligonucleotide of claim 1, wherein the first three and/or the last three nucleotides of said oligonucleotides are 2-O-methylated.

5. The antisense oligonucleotide of claim 1, labeled with a label selected from the group consisting of a fluorescent label, a radioactive label and a metal label.

6. A pharmaceutical composition comprising as active agent at least one antisense oligonucleotide as defined in claim 1.

7. A pharmaceutical composition comprising as active agent a combination of at least two antisense oligonucleotides as defined in claim 1, wherein said combination comprises SEQ ID NO: 1 together with SEQ ID NO: 6 or SEQ ID NO: 1 together with SEQ ID NO: 3 and SEQ ID NO:6.

8. The pharmaceutical composition of claim 6, further comprising buffers, additives, stabilizers, diluents and/or excipients.

9. A method of treating rheumatoid arthritis in a subject, comprising administering to the subject a therapeutically effective amount of an antisense oligonucleotide consisting of the nucleic acid sequence SEQ ID NO: 1, an antisense oligonucleotide consisting of the nucleic acid sequence SEQ ID NO: 3 and an antisense oligonucleotide consisting of the nucleic acid sequence SEQ ID NO: 6, thereby treating rheumatoid arthritis.

* * * * *